US011401439B2

(12) United States Patent
Kashimura et al.

(10) Patent No.: US 11,401,439 B2
(45) Date of Patent: Aug. 2, 2022

(54) MOLDED ARTICLE AND HOLLOW TUBE

(71) Applicant: Hitachi Metals, Ltd., Tokyo (JP)

(72) Inventors: Seiichi Kashimura, Tokyo (JP); Masamichi Kishi, Tokyo (JP); Naoto Teraki, Tokyo (JP); Takanobu Watanabe, Tokyo (JP); Yuriko Kiyokane, Tokyo (JP)

(73) Assignee: HITACHI METALS, LTD, Tokyo (JP)

( * ) Notice: Subject to any disclaimer, the term of this patent is extended or adjusted under 35 U.S.C. 154(b) by 0 days.

(21) Appl. No.: 17/235,695

(22) Filed: Apr. 20, 2021

(65) Prior Publication Data

US 2021/0238446 A1 Aug. 5, 2021

Related U.S. Application Data

(63) Continuation of application No. 17/011,750, filed on Sep. 3, 2020.

(30) Foreign Application Priority Data

Sep. 13, 2019 (JP) .............................. JP2019-167722
Feb. 27, 2020 (JP) .............................. JP2020-031580
Jul. 2, 2020 (JP) .............................. JP2020-114598

(51) Int. Cl.
*C09D 183/04* (2006.01)
*C08K 3/36* (2006.01)
*A61B 1/00* (2006.01)

(52) U.S. Cl.
CPC ........ *C09D 183/04* (2013.01); *A61B 1/00064* (2013.01); *A61L 2420/04* (2013.01); *C08K 3/36* (2013.01)

(58) Field of Classification Search
None
See application file for complete search history.

(56) References Cited

U.S. PATENT DOCUMENTS

| 10,258,765 | B2 | 4/2019 | Kashimura et al. |
| 2007/0299402 | A1 | 12/2007 | Ishii et al. |
| 2016/0148717 | A1 | 5/2016 | Kikuchi et al. |
| 2018/0036509 | A1 | 2/2018 | Kashimura et al. |
| 2019/0352848 | A1 | 11/2019 | Kashimura et al. |
| 2020/0032000 | A1* | 1/2020 | Kitazawa ................. C09D 4/06 |

FOREIGN PATENT DOCUMENTS

| CN | 101107543 A | 1/2008 |
| CN | 106189016 A | 12/2016 |
| CN | 107680724 A | 2/2018 |
| EP | 3569264 A1 | 11/2019 |
| JP | 11-213771 A | 8/1999 |
| JP | 2008-287 A | 1/2008 |
| JP | 2018-23758 A | 2/2018 |

OTHER PUBLICATIONS

Office Action issued in the corresponding Korean Patent Application No. 10-2020-0072699 dated Sep. 28, 2020.
Extended European Search Report issued in the corresponding European Patent Application No. 20181146.0 dated Jan. 14, 2021.
Office Action issued in the corresponding Chinese Patent Application No. 202010561443.3 dated Dec. 7, 2020.
Office Action issued in the corresponding Japanese Patent Application No. 2021-146057 dated Oct. 7, 2021.
Office Action issued in the corresponding European Patent Application No. 20181146.0 dated Oct. 20, 2021.
Office Action issued in the corresponding Chinese Patent Application No. 202110788233.2 dated Jan. 13, 2022.

\* cited by examiner

*Primary Examiner* — Robert T Butcher
(74) *Attorney, Agent, or Firm* — Roberts Calderon Safran & Cole P.C.

(57) ABSTRACT

A coating film is provided in a cable, a medical hollow tube, a molded article and a hollow tube. The coating film is formed from a rubber composition including a rubber component and fine particles. A static friction coefficient on a surface of the coating film is 0.5 or less. When the coating film is subjected to a testing such that a long fiber nonwoven fabric including cotton linters including an alcohol for disinfection with a length of 50 mm along a wiping direction is brought contiguous to the surface of the coating film at a shearing stress of $2 \times 10^{-3}$ MPa to $4 \times 10^{-3}$ MPa, followed by wiping off the surface of the coating film at a speed of 80 times/min to 120 times/min and 20,000 repetitions thereof for a wiping direction length of 150 mm, a difference (an absolute value of a difference) between the static friction coefficients of the coating film before and after the testing is not greater than 0.1.

8 Claims, 14 Drawing Sheets

MOLDED ARTICLE AND HOLLOW TUBE

CROSS-REFERENCE TO RELATED APPLICATION

The present application is a Continuation of U.S. patent application Ser. No. 17/011,750 which is based on Japanese patent application No. 2019-167722 filed on Sep. 13, 2019, Japanese patent application No. 2020-031580 filed on Feb. 27, 2020, and Japanese patent application No. 2020-114598 filed on Jul. 2, 2020 the entire contents of which are incorporated herein by reference.

BACKGROUND OF THE INVENTION

1. Field of the Invention

The present invention relates to a molded article and a hollow tube.

2. Description of the Related Art

JP-A-2008-287 (Patent Document 1) and JP-A-2018-23758 (Patent Document 2) discloses a technique on a medical coating composition, which can impart a stable sliding property to a surface without applying a lubricant to that surface.

[Patent Document 1] JP-A-2008-287
[Patent Document 2] JP-A-2018-23758

SUMMARY OF THE INVENTION

A sheath made of an electrical insulating member is formed on a surface of a cable. This sheath is desired to have no stickiness or the like, but a good slidability (sliding property). On the other hand, an end portion of the cable is subjected to a termination, during which a protective member such as a boot or the like is attached to the sheath with an adhesive. Here, in the cable with the protective member having been attached thereto, for example, when the end portion of the cable is bent, a coating film, which has been formed on a surface of the sheath, may be peeled off, which may lead to the protective member detaching from the cable. That is, the cable is required to have no stickiness or the like but a good slidability on the surface of that cable, and a resistance of the coating film formed on the surface of the sheath to being peeled off.

Also, a medical hollow tube as an example of molded articles is provided with a coating film on an outer surface or an inner surface of a hollow tube main body. As with the coating film of the cable, this coating film of the medical hollow tube is required to have a good slidability, and a resistance of the coating film formed on the outer surface or the inner surface of the hollow tube main body to being peeled off.

From the aspect of good hygiene, on the other hand, it is necessary to keep the surfaces of the molded articles such as the cable or the medical hollow tube clean by wiping off them with a disinfecting alcohol. For that reason, the coating film is required to have such a high resistance to being wiped off as to maintain a high slidability, even when repeatedly wiped off with the disinfecting alcohol or the like.

Accordingly, it is an object of the present invention to provide a technique for allowing a coating film to develop a slidability and a resistance to being wiped off at a high level.

According to one aspect of the present invention, there is provided a molded article, comprising: a molded article main body, and a coating film covering a surface of the molded article main body, the coating film adhering to the molded article main body, wherein the coating film comprises a rubber composition including a rubber component and fine particles, with a static friction coefficient on a surface of the coating film being 0.5 or less, wherein the coating film comprises a resistance to being wiped off in such a manner that, when the coating film is subjected to a testing such that a long fiber non-woven fabric including cotton linters including an alcohol for disinfection with a length of 50 mm along a wiping direction is brought contiguous to the surface of the coating film at a shearing stress of $2\times10^{-3}$ MPa to $4\times10^{-3}$ MPa, followed by wiping off the surface of the coating film at a speed of 80 times/min to 120 times/min and 20,000 repetitions thereof for a wiping direction length of 150 mm, a difference (an absolute value of a difference) between the static friction coefficients of the coating film before and after the testing is not greater than 0.1.

According to another aspect of the present invention, there is provided a hollow tube, comprising: a hollow tube main body including an inner surface and an outer surface; and a coating film covering at least one of the inner surface and the outer surface of the hollow tube main body, the coating film adhering to the hollow tube main body, wherein the coating film comprises a rubber composition including a rubber component and fine particles, with a static friction coefficient on a surface of the coating film being 0.5 or less, wherein the coating film comprises a resistance to being wiped off in such a manner that, when the coating film is subjected to a testing such that a long fiber non-woven fabric including cotton linters including an alcohol for disinfection with a length of 50 mm along a wiping direction is brought contiguous to the surface of the coating film at a shearing stress of $2\times10^{-3}$ MPa to $4\times10^{-3}$ MPa, followed by wiping off the surface of the coating film at a speed of 80 times/min to 120 times/min and 20,000 repetitions thereof for a wiping direction length of 150 mm, a difference (an absolute value of a difference) between the static friction coefficients of the coating film before and after the testing is not greater than 0.1.

Points of the Invention

According to the present invention, it is possible to allow the coating film to develop a slidability and a resistance to being wiped off at a high level.

DETAILED DESCRIPTION OF THE PREFERRED EMBODIMENTS

<Findings Obtained by the Present Inventors>

Figure 1:
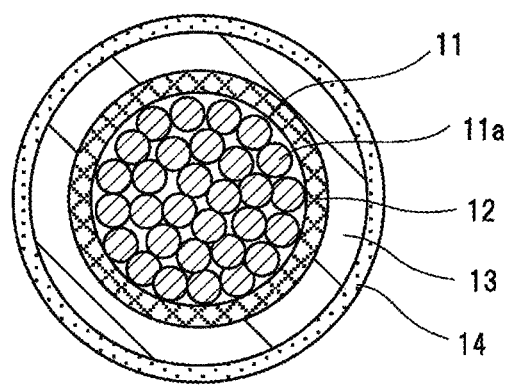
FIG. 1 is a cross-sectional view perpendicular to a length direction of a cable according to one embodiment of the present invention.

First, the findings obtained by the present inventors will be described.

For example, in an ultrasonic imaging device that is designed as a medical device, an ultrasonic probe is connected to a cable, so that a medical test is performed by moving that ultrasonic probe on a human body. At this point of time, if the cable connected to the ultrasonic probe is sticky, the cable may be stuck by being brought into contact with another cable or by being caused to touch a medical tester's garment or the like. As a result, the ultrasonic probe may be difficult to move smoothly, which may lead to impairing the handleability of the medical device.

Conventionally, from the point of view of ensuring the slidability of the cable, a polyvinyl chloride (PVC) has been used as a material for forming a sheath for the cable. It should be noted, however, that, with the PVC, as the period of use of the cable becomes longer, an alteration of the sheath, such as a discoloring of the sheath, is more likely to occur.

From this, in place of the PVC, a silicone rubber being excellent in heat resistance and chemical resistance has been studied as the sheath material. It should be noted, however, that, since the sheath formed of the silicone rubber tends to be sticky (also termed tacky), the sheath formed of the silicone rubber tends to be low in slidability (sliding property).

In view of the foregoing, for the purpose of improving the slidability of the cable, providing a coating film having a small static friction coefficient on a surface of the sheath formed of the silicone rubber has been proposed. As the coating film having a small static friction coefficient, the coating film formed of a rubber composition including fine particles and having micro irregularities produced by the fine particles on its surface has been studied.

However, according to the present inventors' study, it has been found out that the cable provided with the above-described coating film, though having the resulting slidability, has the following two problems.

One of the two problems is that no enough adhesion strength between the coating film and the sheath can be ensured. When the cable is used as, e.g., a probe cable, a boot may be attached to a terminal of the cable as a protective member. At this point of time, the boot is attached to the coating film formed on the outermost surface of the cable with an adhesive between the boot and the coating film. However, the adhesion strength between the underlying sheath and the overlying coating film is low, and therefore, when the boot attached to the cable is acted on by a bending pressure, a peeling off of the coating film may occur at the interface between it and the underlying sheath, which may lead to the boot detaching from the cable.

The other one of the two problems is that the coating film is low in resistance to being wiped off. The cable for medical use is used repeatedly by being wiped off with a disinfecting alcohol or the like to keep its surface clean. According to the present inventors' study, however, it has been found that the irregular state of the coating film surface is changed by the repeating of the wiping off of the coating film surface, which increases the static friction coefficient of the coating film with the increase of the number of times the coating film is wiped off, and which makes it difficult to obtain the desired slidability of the cable. In other words, the coating film may be unable to maintain the slidability of the cable at a high level over a long period of use.

As a result of the study on the above two problems, the present inventors have found out that a factor that degrades the various properties of the coating film is air bubbles present in the coating film. The air bubbles are the ones formed when a liquid material to be used to form the coating film is cured. The presence of these air bubbles in the surface of the coating film to be brought contiguous to the sheath leads to a lessening in the area of the adhesion of the coating film to the sheath, and therefore a lowering in the strength of the adhesion of the coating film to the sheath. Further, on the other hand, the presence of the air bubbles in the surface of the coating film may lead to formation of a collapse (a collapsed portion), and an edge of such a collapsed portion on the surface of the coating film may lead to the occurrence of being stuck at that edge when the surface of the coating film is wiped off. For that reason, the coating film tends to be scraped off during being wiped off, and its slidability is likely to be lowered by the repeating of the wiping off of the coating film surface. Furthermore, the air bubbles disrupt the dense distribution of the fine particles on the surface of the coating film, and greatly affect the irregular state of the coating film surface, and therefore the various properties of the coating film produced by the irregularities on the surface of the coating film.

From these points, as a result of the study to reduce the air bubbles (voids) present in the coating film by suppressing the formation of the air bubbles when the coating film is cured and formed, the present inventors have found out that it is possible to allow the coating film to achieve its slidability, adhesion strength and resistance to being wiped off at a high level and in a well-balanced manner.

The present invention has been made based on the above findings.

One Embodiment of the Present Invention

Hereinafter, one embodiment of the present invention will be described by taking a medical device cable, which is configured to be connectable to a medical device, as one example, and by using the drawings. Note that, in all the drawings for describing the embodiment, the same members are denoted by the same reference characters in principle, and the repeated descriptions thereof will be omitted. Further, hatching may be used even in a plan view to make the drawings easy to understand.

[Cable]

As shown in FIG. 1, a medical device cable 10 of the present embodiment (hereinafter, also referred to as simply the cable 10) is configured in such a manner that a sheath 13 and a coating film 14 are in turn stacked over an outer periphery of a cable core 11.

(Cable Core)

The cable core 11 is constituted by laying a plurality of electric wires 11a together and coating an outer periphery of the plurality of electric wires 11a laid together with a shield 12. Examples of the electric wire 11a to be able to be used include: an electric wire composed of a conductor made of a solid wire or a stranded wire such as a pure copper wire or a tin-plated copper wire or the like, and an electrical insulating member covering an outer periphery of that conductor, a coaxial cable, an optical fiber, and the like. As the shield 12, for example, a braided wire or the like can be used.

(Sheath)

The sheath 13 is formed of an electrical insulating material, and is covering the cable core 11. The electrical insulating material is not particularly limited as long as it is capable to be used in the sheath 13, but examples of the electrical insulating material to be able to be used include: a silicone rubber, a polyethylene, a chlorinated polyethylene, a chloroprene rubber, a polyvinyl chloride (PVC), and the like. Among them, the silicone rubber or the chloroprene rubber is preferable from the point of view of the chemical resistance and the heat resistance. Note that the electrical insulating material to form the sheath may be added with general compounding agents such as each type of crosslinking agents, crosslinking catalysts, antioxidants, plasticizers, lubricants, fillers, flame retardants, stabilizers, coloring agents and the like.

(Coating Film)

The coating film 14 is covering the sheath 13. The coating film 14 is formed from a rubber composition including fine particles and a rubber component, and is configured in such a manner that the fine particles are finely dispersed in the rubber component. A surface of the coating film 14 is formed with irregularities derived from the fine particles. The above irregularities on the surface of the coating film 14 are able to make small the contact area of the coating film 14 when the coating film 14 is brought into contact with another member, and are therefore able to make the static friction coefficient of the coating film 14 smaller than the static friction coefficient inherent in the rubber component constituting the coating film 14. This coating film 14 is capable to make the slidability of the cable 10 high as compared with the case where the sheath 13 is present at the surface of the cable 10.

The static friction coefficient of the coating film 14 is not particularly limited, but is preferably 0.5 or less from the point of view of imparting the desired slidability to the cable 10.

Also, since the fine particles are densely distributed on the surface of the coating film 14, the coating film 14 is high in the resistance to being wiped off. Specifically, when the coating film 14 is subjected to a testing such that a long fiber non-woven fabric including cotton linters including a disinfecting alcohol (hereinafter, also referred to as "cotton cloth") with a length of 50 mm along a wiping direction is brought contiguous to the surface of the coating film at a shearing stress of $2\times10^{-3}$ MPa to $4\times10^{-3}$ MPa, followed by wiping off the surface of the coating film 14 at a speed of 80 times/min to 120 times/min (40 cycles/min to 60 cycles/min) and 20,000 repetitions (10,000 cycles) thereof for a wiping direction length of 150 mm, a difference (an absolute value of a difference) between the static friction coefficients of the coating film before and after the testing can be reduced to not greater than 0.1, preferably not greater than 0.05. That is, even when the coating film 14 is repeatedly wiped off, its surface irregularities can be maintained, and the slidability produced by the surface irregularities of the coating film 14 can be maintained over a long period of time. Here, a "cotton cloth length" is a length of the cotton cloth along the wiping direction, and a "wiping direction length" is a length of a part of the cable sheath on which complete wiping is performed by moving the cotton cloth when the surface of the coating film 14 is wiped off with the cotton cloth. The "shearing stress" is a pulling force (a resistance in pulling out) generated when pulling out the cable from the cotton cloth while pressing the cable by the cotton cloth impregnated with the disinfecting alcohol.

An amount of the disinfecting alcohol to impregnate the cotton cloth should be equal to or more than an amount enough for spreading entirely over the cotton cloth. For example, in general, the amount of the disinfecting alcohol to impregnate a surgical gauze is 5 ml to 6 ml per 1 g of the cotton cloth. Since the weight (size) of the cotton cloth depends on an outer diameter of the cable to be wiped off, the weight of the cotton cloth to be used is previously measured and the impregnation amount is adjusted in accordance with the measured weight. For example, when a cable with an outer diameter of 6.7 mm is used, a cotton cloth ("BEMCOT regular type (M-3II)" available from Asahi Kasei Corporation) with a weight of approximately 0.25 g to 0.30 g is required, it is preferable that the cotton cloth is impregnated with an amount of 2.0 ml of the disinfecting alcohol which sufficiently satisfies the above standard.

In addition, in the present embodiment, as will be described in detail later, since the formation of the air bubbles during the curing of the rubber composition is suppressed, the air bubbles (voids) present in the coating film 14 can be reduced. For that reason, it is possible to suppress a decrease in the contact area of the sheath 13 side surface of the coating film 14 due to the air bubbles (voids). This allows the contact area between the overlying coating film 14 and the underlying sheath 13 to be held large, and the adhesion strength between the overlying coating film 14 and the underlying sheath 13 to be made higher than when the air bubbles are present in the coating film 14. Specifically, the adhesion strength between the overlying coating film 14 and the underlying sheath 13 can be set at not lower than 0.3 MPa. Note that the upper limit of the adhesion strength between the underlying sheath 13 and the overlying coating film 14 is not particularly limited, but, in practice, is on the order of 0.7 MPa.

Further, since the air bubbles can be reduced also in the frontside (upper) surface of the coating film 14, the occurrence of a collapse formation due to the air bubbles can be reduced in the frontside (upper) surface of the coating film 14. Since no fine particles can be present at the collapse formation part of the coating film 14, the occurrence of a collapse formation leads to a lessening in the region of the coating film 14 where the fine particles can be distributed. This leads to a lessening in the number of the fine particles distributed on the surface of the coating film 14. That is, the distribution of the fine particles becomes sparse. In addition, since a plurality of the fine particles easily aggregate to form coarse aggregated particles, it is difficult to produce the desired surface irregularities. On the other hand, by reducing the occurrence of a collapse formation, it is possible to increase the number of the fine particles occupying the surface of the coating film 14, or suppress the occurrence of an aggregation of the fine particles, and it is therefore possible to more densely distribute the fine particles on the surface of the coating film 14.

Also, since the fine particles are densely distributed on the surface of the coating film 14, there is little variation in the number of the fine particles by region. Specifically, it is preferable that, when the number of the fine particles per unit area is measured in any plurality of parts of the surface of the coating film 14, a number distribution, which is calculated from a formula $(N_{max}-N_{min})/(N_{max}+N_{min})\times 100$ where $N_{max}$ is a maximum value of the number of the fine particles per unit area and $N_{min}$ is a minimum value of the number of the fine particles per unit area, is 5% or less. The smaller the number distribution, the smaller the deviation in the number of the fine particles, which indicates that the variation in the distribution of the fine particles is lessened.

In addition, it is preferable that the number of voids, which are formed by the air bubbles, is lessened in the surface of the coating film 14, and it is preferable that substantially no void is present in the surface of the coating film 14. Specifically, when observed with an electron microscope SEM in a condition of a magnification of 1000 times, the number of voids having a size of not smaller than 1 μm present per unit area is preferably not more than 5/40 μm square, and more preferably, substantially no void having a size of 10 μm or more is present in the surface of the coating film 14.

On the surface of the coating film 14, the number of collapsed portions present, which are formed by the voids, may be lessened, while the number of projecting portions present, which are formed by the fine particles, may be increased. That is, it is preferable that the surface of the coating film 14 has the surface irregularities formed principally from the projecting portions.

The thickness of the coating film 14 is not particularly limited, but is preferably not thinner than 3 μm and not thicker than 100 μm. When the thickness of the coating film 14 is set at not thinner than 3 μm, the predetermined resistance to being wiped off can be imparted to the coating film 14. Further, when the thickness of the coating film 14 is set at not thicker than 100 μm, the flexibility or bendability of the cable 10 can be held high.

(Rubber Composition for Coating Film Formation)

Next, the rubber composition for forming the coating film 14 will be described.

The rubber composition is a cured product, which is produced by curing a liquid rubber composition (hereinafter, also referred to as the coating material) including a liquid rubber, fine particles, a curing catalyst, and, if desired, other additives, and the rubber component is configured to include the cured rubber component and the fine particles.

The rubber component is a matrix component constituting the coating film 14. A silicone rubber can be used as the rubber component. There are two types of silicone rubbers: a condensation reaction type silicone rubber and an addition reaction type silicone rubber, depending on curing methods, but among them, the addition reaction type silicone rubber is preferable. The addition reaction type silicone rubber is resistant to producing the air bubbles during curing as compared with the condensation reaction type silicone rubber, and is therefore able to make the distribution of the fine particles in the coating film 14 denser.

The addition reaction type silicone rubber is produced by curing a liquid silicone rubber composition by an addition reaction. The liquid silicone rubber composition contains, for example, an organopolysiloxane having a vinyl group ($CH_2$=CH—) and an organohydrogen polysiloxane having a hydrosilyl group (Si—H). The organopolysiloxane serves as a base polymer for the silicone rubber. The organohydrogen polysiloxane serves as a crosslinking agent for the base polymer. For example, by mixing a platinum catalyst, the organohydrogen polysiloxane undergoes a hydrosilylation reaction between the hydrosilyl group and the vinyl group in the base polymer, thereby crosslinking and curing the base polymer. The organopolysiloxane and the organohydrogen polysiloxane are not particularly limited, but the conventionally known organopolysiloxane and organohydrogen polysiloxane can be used.

Also, a chloroprene rubber may be used as the rubber component, and the coating film 14 may be configured to include the chloroprene rubber.

The fine particles are dispersed in the rubber component to form the projecting portions, which are formed on the surface of the coating film 14. As the fine particles, it is preferable to use at least any fine particles of silicone rubber fine particles, silicone resin fine particles and silica fine particles. The types of the fine particles can be appropriately altered according to the required properties of the coating film 14.

Specifically, it is preferable that the fine particles have a higher hardness than that of the coating film 14 from the point of view of maintaining the surface irregularities shape of the coating film 14 and ensuring the slidability of the coating film 14 when an object is brought into contact with the coating film 14. Specifically, it is preferable that the fine particles have a Shore (durometer A) hardness of not lower than 1.1 times the hardness of the cured product constituting the coating film 14. This is because the higher the hardness of the fine particles, the more resistant the fine particles are to being deformed by the pressing pressure when an object is brought into contact with the surface of the coating film 14, and the more easily the surface irregularities shape of the coating film 14 is maintained. Since the hardness becomes high in the order of the silicone rubber, the silicone resin, and the silica, the silica fine particles are preferred from the point of view of the hardness.

On the other hand, from the point of view of uniformly distributing the fine particles on the surface of the coating film 14 and forming the desired surface irregularities of the coating film 14, the fine particles are preferably small in mass. This is because if the fine particles are large in mass, the fine particles settle before the coating material is cured to form the coating film 14, so the fine particles become resistant to forming the moderate irregularities on the surface of the coating film 14. In this regard, by making the fine particles small in mass, the settling of the fine particles is suppressed, and the moderate irregularities are easily formed on the surface of the coating film 14. Since the mass becomes large in the order of the silicone rubber, the silicone resin, and the silica, the silicone rubber particles are preferable from the point of view of the mass.

Namely, the silicone resin fine particles are preferable from the point of view of both maintaining the surface irregularities shape of the coating film 14 to ensure the slidability of the surface of the coating film 14, and uniformly distributing the fine particles on the surface of the coating film 14 to easily form the desired surface irregularities of the coating film 14.

The quantity of the fine particles to be contained in the rubber composition is preferably not lower than 10% by mass and not higher than 60% by mass. By setting the quantity of the fine particles to be contained in the rubber composition at not lower than 10% by mass, it is possible to form the irregularities on the surface of the coating film 14, so it is possible to make the static friction coefficient of the coating film 14 small and thereby impart the desired slidability to the surface of the coating film 14. On the other hand, if the quantity of the fine particles to be contained in the rubber composition is excessively large, the strength of the coating film 14 may be lowered, but, by setting the quantity of the fine particles to be contained in the rubber composition at not higher than 60% by mass, it is possible to maintain the strength of the coating film 14 while obtaining the slidability of the surface of the coating film 14. Note that the quantity of the fine particles to be contained in the rubber composition is calculated on the assumption that the coating material is cured with substantially no decrease in mass, and refers to the proportion of the fine particles to the cured coating film 14 (the total of the rubber component and the fine particles). In other words, the content of the fine particles is preferably 10% by mass to 60% by mass of the total of the rubber component and fine particles.

The sizes of the fine particles may be appropriately altered according to the thickness of the coating film 14, and are not particularly limited. From the point of view of forming the desired irregularities on the surface of the coating film 14, the average particle diameter of the fine particles is preferably 1 μm or more and 10 μm or less. Here, the average particle diameter refers to the one measured by a laser diffraction scattering method. By setting the average particle diameter of the fine particles at not smaller than 1 μm, it is easy to form the moderate irregularities on the surface of the coating film 14, so it is possible to make the static friction coefficient of the coating film 14 small and thereby make the slidability of the coating film 14 higher. Moreover, since the masses of the fine particles can be adjusted to an appropriate magnitude by setting the average particle diameter of the fine particles at not larger than 10 μm, it is possible to suppress the occurrence of a settling of the fine particles and the occurrence of an uneven coating during coating with the liquid rubber composition.

The curing catalyst is not particularly limited as long as it is capable to promote the addition reaction, but, for example, a platinum or a platinum-based compound may be used as the curing catalyst.

The other additives may be compounded if desired. For example, an organic solvent can be used for the purpose of adjusting the viscosity of the coating material. Examples of the organic solvent to be able to be used include: aromatic hydrocarbon-based solvents such as toluene, xylene and the like, and aliphatic hydrocarbon-based solvents such as n-hexane, n-heptane, n-octane, isooctane, nonane, decane, undecane, dodecane and the like. The above organic solvents can be used alone or in combination of two or more. Further, for example, alcohols such as ethanol, isopropyl alcohol and the like, or acetone can be used as the organic solvent.

The viscosity of the coating material is not particularly limited, but is preferably not lower than 1 mPa·s and not higher than 100 mPa·s from the point of view of densely distributing the fine particles. When the viscosity of the coating material is within the above range, it is possible to appropriately alter the thickness of the coating film 14 as well. Note that the viscosity of the coating material is measured at a temperature of 25±2 degrees C. using a tuning fork vibrating viscometer (SV—H, available from A & D Corporation).

Furthermore, for example, it is preferable to add a fumed silica having a smaller particle diameter than those of the fine particles to the rubber composition from the point of view of forming the desired irregularities on the surface of the coating film 14. The fumed silica is produced by burning a raw material silicon chloride at a high temperature, and refers to ultrafine silica particles having an average primary particle diameter of e.g. not smaller than 10 nm and not larger than 30 nm. The fumed silica is classified into a hydrophilic fumed silica having a silanol group (Si—OH) on its surface and a hydrophobic fumed silica produced by chemically reacting the silanol group on its surface, but both the hydrophilic fumed silica and the hydrophobic fumed silica can be used. The fumed silica is excellent in dispersibility in the coating material and contributes to enhancing the dispersibility of the fine particles in the coating material. As a result, the settling of the fine particles in the coating material can be suppressed, and therefore the desired irregularities can be formed on the surface of the coating film 14.

The quantity of the fumed silica to be contained in the rubber composition is not particularly limited, but is preferably not lower than 0.1% by mass and 0.5 or less % by mass. Note that, herein, the quantity of the fumed silica to be contained in the rubber composition, is calculated in the same manner as the case of the fine particles, on the assumption that the coating material is cured with substantially no decrease in mass, and refers to the proportion of the fumed silica to 100 parts by mass of the cured rubber component.

[Cable Producing Method]

Next, a method for producing the above-described cable 10 will be described.

First, a plurality of (e.g., 100 or more) electric wires 11a such as coaxial cables or the like are bundled together. For example, a braided shield is formed as the shield 12 to coat the bundle of the plurality of electric wires 11a. This results in the cable core 11.

Next, the sheath material including, for example, the silicone rubber is extruded to coat the surface of the cable core 11 to form the sheath 13 thereon.

From the viewpoint of increasing the adhesion between the coating film 14 and the sheath 13, it is preferable to add an infrared absorber to a material of the sheath. By the addition of the infrared absorber, when the coating film 14 is heated by a heater, the sheath 13 absorbs more infrared rays and is more easily heated from the side of the sheath 13. Therefore, in the coating of the rubber composition, it is possible to reduce the uneven curing in the thickness direction and accelerate the curing a deep part distant from the surface (i.e. a part closer to the sheath 13). As a result, the adhesion strength between the coating film 14 thus obtained and the sheath 13 can be further increased. In addition, it is possible to shorten the time for curing the coating of the rubber composition by heating.

The infrared absorber is not specifically limited, and e.g. CoO, $Fe_2O_3$, $MnO_2$, $Cr_2O_3$, CuO, NiO, $TiO_2$ (oxidized titanium), C (carbon) and the like may be used.

The content of the infrared absorber is not particularly limited, as long as the performance of the sheath is not significantly deteriorated. From the viewpoint of increasing the adhesion between the coating film 14 and the sheath 13, the content of the infrared absorber is preferably 0.1% by mass or more. Meanwhile, if the content of the infrared absorber is excessively large, the sheath 13 will be fragile so that the tear strength may be deteriorated. Therefore, from the viewpoint of maintaining high tear strength, the content of the infrared absorber is preferably 10% by mass or less. Note that the content of the infrared absorber is the proportion of the infrared absorber to 100 parts by mass of the sheath material.

Next, the coating material is applied to the surface of the sheath 13 to form a coating material layer thereon. The method for applying the coating material is not particularly limited, but may be appropriately selected from, for example, a dipping method, a spray coating method, a roll coating method and the like. Among these, the dipping method is preferred.

The dipping method is designed as the method of forming the coating material layer on the surface of the sheath 13 by, e g , immersing a wire rod formed with the sheath 13 thereon in the coating material and pulling up that wire rod. Since the dipping method is capable to make the thickness of the coating material layer uniform, the film thickness of the coating film 14 can be formed uniformly in a length direction of the wire rod. In addition, by adjusting the pulling up speed for the cable 10, the distribution of the fine particles in the coating film 14 can be more densely controlled. Hereinafter, this point will be described.

In the dipping method, when the cable 10 is pulled up from the liquid level of the coating material, the coating material adheres to the surface of the cable 10. When the coating material adheres to the surface of the cable 10, the fine particles may be moving and self-ordering in the coating material layer. This self-ordering allows the fine particles to be densely distributed on the surface of the coating material layer. And, the slower the cable pulling up speed, the more the time to be able to be ensured for the self-ordering of the fine particles, and the more stably the densely distributed state of the fine particles can be reproduced.

Specifically, from the point of view of densely dispersing the fine particles, the pulling up speed for the cable 10 is preferably not higher than 10 m/min, more preferably not higher than 5 m/min. On the other hand, from the point of view of the productivity of the coating film 14, it is preferable to set the pulling up speed for the cable 10 at not lower than 1 m/min. In other words, by setting the pulling up speed for the cable 10 at not lower than 1 m/min and not higher than 5 m/min, it is possible to make the distribution of the fine particles in the surface of the coating film 14 denser while maintaining the productivity of the coating film 14.

Next, the coating material layer is dried and cured by heating to form the coating film 14 having the predetermined surface irregularities. The heating temperature is not particularly limited, but may be set at, for example, 120 degrees C. to 200 degrees C.

In heating of the coating, it is preferable to use an infrared heater when the infrared absorber is added to the sheath 13.

By heating the coating with the use of the infrared heater, it is possible to accelerate the heating of the sheath 13 and to suppress the uneven curing in the thickness direction of the coating film 14 to be obtained. As a result, the adhesion strength between the coating film 14 and the sheath 13 can be further increased. In addition, it is possible to shorten the time for curing the coating until the coating film 14, thereby improve the producibility of the cable 10.

This results in the cable 10 of the present embodiment.

[Probe Cable]

Figure 2A:
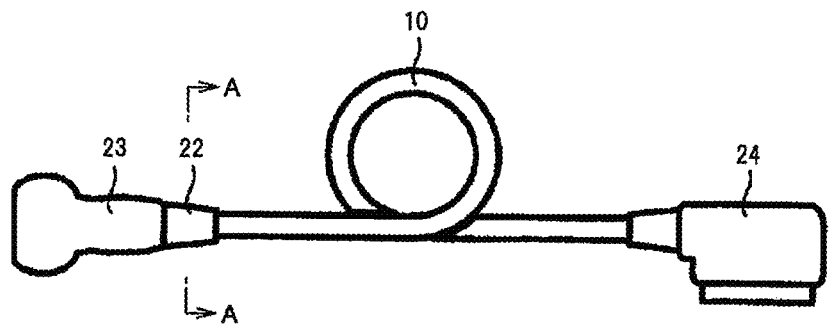
FIG. 2A is a diagram schematically showing a probe cable configured to be connectable to an ultrasonic imaging device.
Figure 2B:
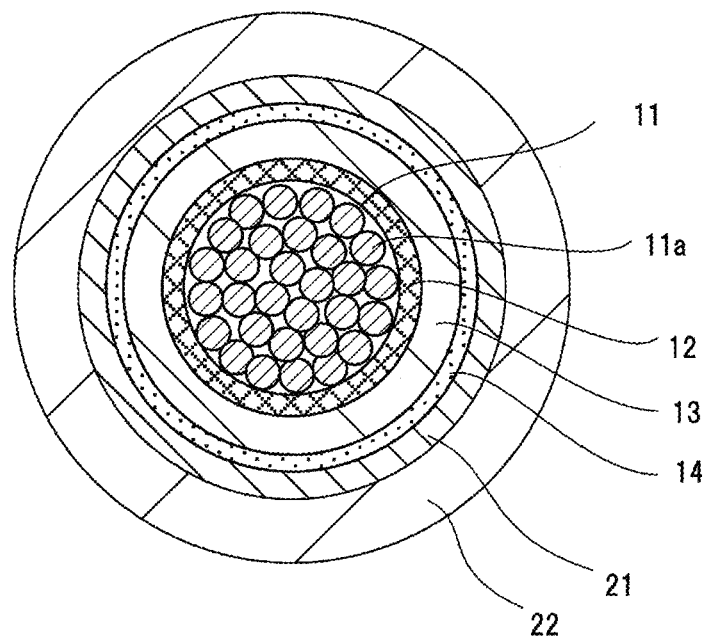
FIG. 2B is a cross-sectional view showing the probe cable taken along line A-A of FIG. 2A.

As shown in FIG. 2A, for example, a probe cable 20 is configured in such a manner that an ultrasonic probe terminal 23 (hereinafter, also referred to as simply a terminal 23) and a protective member 22 for protecting that terminal 23 are attached to one end of the cable 10, while a connector 24 is attached to the other end of the cable 10. The terminal 23 is connected to, for example, an ultrasonic probe, while the connector 24 is connected to, for example, a main body portion of the ultrasonic imaging device. The protective member 22 is a so-called boot, and as shown in FIG. 2B, is fitted over the coating film 14 to cover the coating film 14 with an adhesion layer 21 therebetween. The adhesion layer 21 is formed of, for example, a silicone based adhesive or an epoxy-based adhesive.

Advantageous Effects of the Present Embodiment

According to the present embodiment, one or more of the following advantageous effects are achieved.

(a) In the cable 10 of the present embodiment, the coating film 14 made of the rubber composition including the rubber component and the fine particles is provided on the surface of the sheath 13. At this point of time, the addition reaction type silicone rubber is used as the rubber component. The addition reaction type silicone rubber is capable to lessen the number of the air bubbles formed during the curing reaction, as compared with the condensation reaction type silicone rubber. This makes it possible to suppress the formation of voids, which are derived from the air bubbles, in the surface of the coating film 14 being contiguous to the sheath 13. As a result, the area where the coating film 14 is in contact with the sheath 13 can be maintained without being reduced, and the high adhesion strength between the overlying coating film 14 and the underlying sheath 13 can be ensured. In addition, it is possible to allow the adhesion strength between the underlying sheath 13 and the overlying coating film 14 to be not lower than 0.30 MPa, without forming the surface of the sheath 13 with a special layer for enhancing the adhesion strength between the overlying coating film 14 and the underlying sheath 13, (such as, for example, an adhesion strength reinforcing layer made of a primer or a silane coupling agent or the like, a layer having its surface modified by a method that performs a flame treatment that exposes the surface to flame for a short time, or a method that performs a plasma treatment that ionizes or radicalizes a gas and allows the ionized or radicalized gas to collide with the surface, or a method that performs a corona treatment that ionizes air components in atmospheric discharge and exposes the surface to the ionized air components, or the like), before the formation of the coating film 14. It should be noted, however, that the foregoing does not exclude the provision of the above special layer in order to further increase the adhesion strength between the overlying coating film 14 and the underlying sheath 13. Further, since the addition reaction type silicone rubber also allows the number of voids in the coating film 14 to be reduced, the advantageous effect of enhancing the strength of the coating film 14 itself as well can be expected.

(b) In addition, since the formation of voids in the surface of the coating film 14 can be suppressed, the number of the fine particles occupying the surface of the coating film 14 can be increased, or the occurrence of an aggregation of the fine particles can be suppressed, and so the fine particles can be more densely distributed on the surface of the coating film 14. This makes it possible to form the desired irregularities on the surface of the coating film 14, therefore making the static friction coefficient of the coating film 14 smaller than that of the sheath 13 to be able to achieve the high slidability of the coating film 14.

(c) Moreover, since the collapse formation on the surface of the coating film 14 due to the void formation is lessened, when the surface of the coating film 14 is repeatedly wiped off with a cotton cloth or the like, it is possible to prevent the cotton cloth from being stuck at the edge of the collapse and damaging the coating film 14. This makes it possible to keep the static friction coefficient on the surface of the coating film 14 small even when the surface of the coating film 14 is repeatedly wiped off, and therefore makes it possible to achieve the high resistance of the surface of the coating film 14 to being wiped off. Specifically, when the coating film 14 is subjected to a testing such that the cotton cloth including a disinfecting alcohol (with a length of 50 mm along a wiping direction) is brought contiguous to the surface of the coating film at a shearing stress of $2 \times 10^{-3}$ MPa to $4 \times 10^{-3}$ MPa, followed by wiping off the surface of the coating film 14 at a speed of 80 times/min to 120 times/min (40 cycles/min to 60 cycles/min) and 20,000 repetitions (10,000 cycles), a difference (an absolute value of a difference) between the static friction coefficients of the coating film before and after the testing can be reduced to not greater than 0.1, preferably not greater than 0.05.

(d) Further, the coating film 14 is preferably formed by the dipping method using the coating material including the liquid rubber and the fine particles. The dipping method makes it possible to, when the cable 10 is pulled out from the liquid surface of the coating material to thereby allow the coating material to adhere to the surface of the cable 10, the self-ordering of the fine particles in the coating material can be promoted, and the fine particles can therefore be more densely distributed on the surface of the coating film 14.

(e) In addition, in the dipping method, it is preferable that the pulling up speed for the cable 10 be set at not lower than 1 m/min and not higher than 10 m/min. By pulling up the cable 10 at the speed of not lower than 1 m/min and not higher than 10 m/min, the time taken for the self-ordering of the fine particles can be ensured, and the productivity of the coating film 14 can be kept high. This makes it possible to more densely distribute the fine particles on the surface of the coating film 14.

(f) The static friction coefficient on the surface of the coating film 14 is 0.5 or less, preferably not higher than 0.3, and more preferably not higher than 0.22. In the present embodiment, by forming the irregularities on the surface of the coating film 14, the static friction coefficient on the surface of the coating film 14 can be made smaller than the static friction coefficient inherent in the rubber component constituting the coating film 14, and can be reduced to 0.5 or less. By setting the static friction coefficient on the surface of the coating film 14 at 0.5 or less, it is possible to achieve the high slidability such that the cable 10 is not stuck when being brought into contact with another cable 10.

(g) Since the fine particles are densely distributed on the surface of the coating film 14, the numbers of the fine particles distributed in each of a plurality of locations optionally selected on the surface of the coating film 14 are not greatly different from each other, and the variations in the numbers of the fine particles distributed in each of the plurality of locations are lessened. Specifically, when the number of the fine particles per unit area is measured in any plurality of parts of the surface of the coating film 14, the number distribution, which is calculated from the formula $(N_{max}-N_{min})/(N_{max}+N_{min}) \times 100$ where $N_{max}$ is the maximum value of the number of the fine particles per unit area and $N_{min}$ is the minimum value of the number of the fine particles per unit area, is preferably not more than 5%. By distributing the fine particles densely and uniformly on the surface of the coating film 14 in this manner, the slidability of the coating film 14 and the resistance of the coating film 14 to being wiped off can be made higher.

(h) In the surface of the coating film 14, the number of the voids having a size of not smaller than 1 μm per unit area is preferably not more than 5/40 μm square, and more preferably, there is substantially no void having such a size as to be able to be measured with the electron microscope. By lessening the number of the voids, the fine particles can be more densely distributed on the surface of the coating film 14, and so the slidability of the coating film 14 and the resistance of the coating film 14 to being wiped off can be made higher.

(i) In the coating film 14, since the collapsed portion due to the collapse formation can be suppressed, the surface irregularities can be configured principally with the projecting portions formed by the fine particles. This makes it possible to make the resistance of the coating film 14 to being wiped off high. Hereinafter, this point will be specifically described.

Figure 3A:
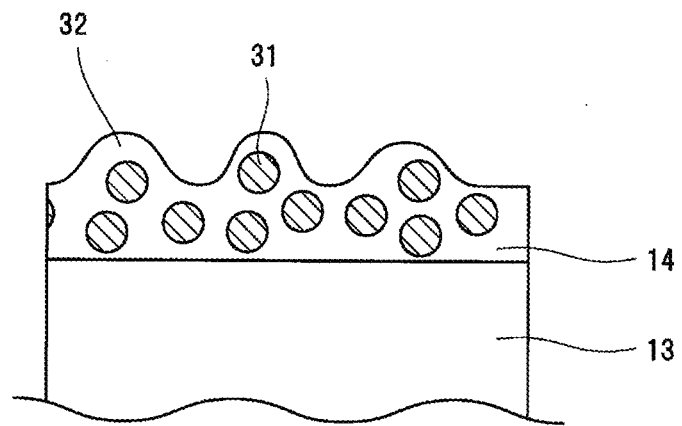
FIG. 3A is a cross-sectional view schematically showing a surface of a coating film in the cable of one embodiment of the present invention.
Figure 3B:
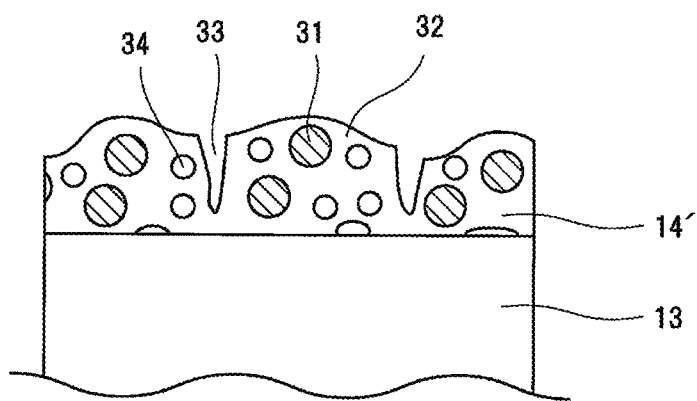
FIG. 3B is a cross-sectional view schematically showing a surface of a coating film in a cable of a comparative example to the present invention.

For example, as shown in FIG. 3B, when the coating film 14' is formed of the condensation reaction type silicone rubber, voids 34 derived from the air bubbles are formed in the coating film 14'. When these voids 34 are present in the surface, collapses 33 (collapsed portions 33) are formed. In that coating film 14', when that coating film 14' is wiped off with a cotton cloth, the cotton cloth tends to be stuck at the edges of the openings of the collapses 33. When the cotton cloth is stuck, the coating film 14' is scraped off, and the repetitions of the scraping off of the coating film 14' cause the desorption of the fine particles 31 from the coating film 14', and the subsequent gradual removal of the projecting portions 32 of the coating film 14'. As a result, the static friction coefficient of the coating film 14' fails to be kept small, and the slidability of the coating film 14' is gradually impaired.

On the other hand, as shown in FIG. 3A, by suppressing the occurrence of the collapse formation due to the void formation in the surface of the coating film 14, it is possible to increase the number of the projecting portions 32 formed by the fine particles 31. This coating film 14, though having the surface irregularities, is resistant to the occurrence of the deep collapse formation, and is therefore able to suppress the occurrence of the cotton cloth being stuck, and keep the static friction coefficient of the coating film 14 small even when the coating film 14 is repeatedly wiped off. That is, the resistance of the coating film 14 to being wiped off can be made higher.

(j) The fine particles 31 are preferably higher in hardness than the rubber component forming the coating film 14. The above fine particles 31 make it easy to maintain the surface irregularities shape of the coating film 14, and therefore make it possible to achieve the desired slidability of the coating film 14.

(k) As the fine particles 31, it is preferable to use at least any fine particles of the silicone resin fine particles, the silicone rubber fine particles and the silica fine particles. The silica fine particles are high in the hardness, and therefore make it easy to ensure the slidability of the coating film 14. Further, the silicone rubber fine particles are relatively small in mass, and are therefore resistant to settling during coating with the coating material, and able to form the moderate irregularities on the surface of the coating film 14. The silicone resin fine particles are intermediate in both the hardness and the mass between the silicone rubber fine particles and the silica fine particles, and therefore make it easy to form the desired surface irregularities shape, and also make it easy to maintain the surface irregularities shape and ensure the slidability of the coating film 14.

(l) Further, the rubber composition preferably further contains the fumed silica. The fumed silica is capable to suppress the occurrence of the settling of the fine particles in the coating material, and therefore makes it possible to form the coating film 14 having its slidability, adhesion strength and resistance to being wiped off at a high level and in a well-balanced manner.

(m) Still further, it is preferable that the sheath 13 further includes an infrared absorber. By the addition of the infrared absorber, when the rubber composition is heated by the infrared heater, the sheath 13 absorbs more infrared rays and the rubber composition is more easily heated from the side of the sheath 13. Therefore, it is possible to suppress the uneven curing in the thickness direction of the coating film 14, thereby further improve the adhesion strength between the coating film 14 and the sheath 13.

(n) In the probe cable 20, the protective member 22 is fitted over the coating film 14 at one end of the cable 10 with the adhesion layer 21 between it and the coating film 14. In the present embodiment, since the adhesion strength between the overlying coating film 14 and the underlying sheath 13 can be made high, for example even when the protective member 22 is acted on by a bending pressure, it is possible to suppress the occurrence of a peeling of the coating film 14 from the sheath 13 and a subsequent detaching of the protective member 22. In addition, since the coating film 14 having the irregularities on its surface is excellent in the slidability, for example when the ultrasonic probe connected to the probe cable 20 is moved, and even if the probe cable 20 is brought into contact with another probe cable 20, it is possible to suppress the occurrence of being stuck. Further, since the coating film 14 is excellent in the resistance to being wiped off, even when the coating film 14 is repeatedly wiped off with a cotton cloth, it is possible to suppress the occurrence of damage or abrasion to the coating film 14, and maintain the slidability of the coating film 14 over a long period of time. Further, since the coating film 14 formed of the silicone rubber is excellent in chemical resistance and heat resistance, even when the coating film 14 is cleaned with a chemical such as a disinfecting alcohol or the like or heated, the alteration in the properties of the coating film 14 can be suppressed.

Other Embodiments

In the above embodiment, the case where the coating film 14 is provided on the probe cable 20 has been described, but the present invention is not limited to this. For example, a medical cable other than the probe cable 20 (such as an endoscope cable or a connection cable for a catheter) or a cabtire cable or the like can also be provided with the above-described coating film.

Further, although the case where the coating film 14 is provided on the surface of the sheath 13 of the cable 10 has been described, the present invention is not limited to this. The present invention is in particular effective for and applicable to a molded article with a surface which is required to be kept clean by wiping off with a disinfecting alcohol or the like from the aspect of good hygiene. For example, molded articles include a handrail (hand hold), a strap, a touch panel, a touch panel protecting film, and a medical hollow tube such as a catheter and the like. Further, the coating film 14 can be applied to a hollow tube such as an air tube to be used a sliding part of a robot or a mobile part of a cable veyor (trademark), water tube as well as the medical hollow tube such as a catheter or the like. Hereinafter, a specific description of the case where the coating film 14 is applied to a medical hollow tube as a molded article will be given with reference to the drawings.

Figure 4A:
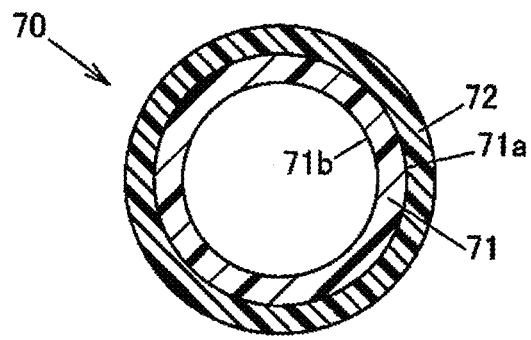
FIG. 4A is a cross-sectional view showing a medical hollow tube provided with an outer coating film on an outer surface of a hollow tube main body.
Figure 4B:
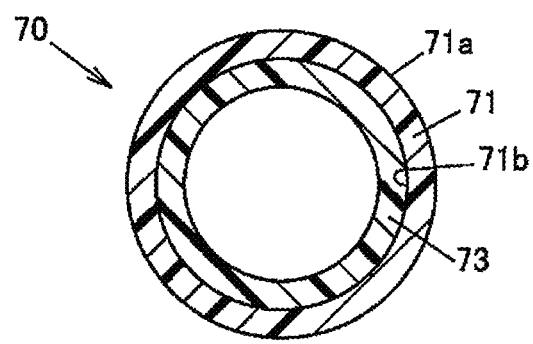
FIG. 4B is a cross-sectional view showing a medical hollow tube provided with an inner coating film on an inner surface of a hollow tube main body.
Figure 4C:
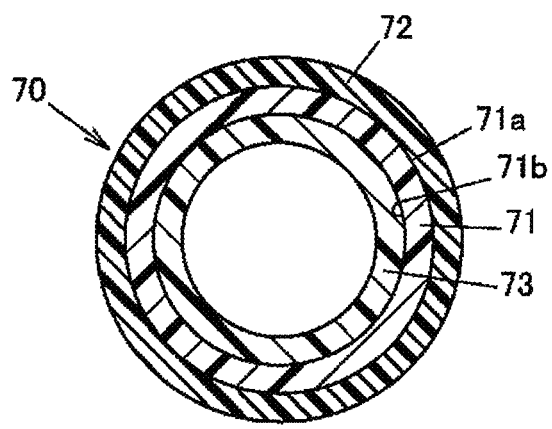
FIG. 4C is a cross-sectional view showing a medical hollow tube provided with an outer coating film and an inner coating film on an outer surface and an inner surface, respectively, of a hollow tube main body.

FIG. 4A is a cross-sectional view showing a medical hollow tube 70 provided with an outer coating film 72 on an outer surface 71a of a hollow tube main body 71. FIG. 4B is a cross-sectional view showing the medical hollow tube 70 provided with an inner coating film 73 on an inner surface 71b of the hollow tube main body 71. FIG. 4C is a cross-sectional view showing the medical hollow tube 70 provided with the outer coating film 72 and the inner coating film 73 on the outer surface 71a and the inner surface 71b, respectively, of the hollow tube main body 71.

The medical hollow tube 70 is configured to include a hollow tube main body 71, and an outer coating film 72 and/or an inner coating film 73 that is covering a circumference (an outer surface 71a or an inner surface 71b or both the outer surface 71a and the inner surface 71b) of the hollow tube main body 71, the coating film adhering to the hollow tube main body 71. The hollow tube main body 71 may be formed of, for example, a silicone rubber. The outer coating film 72 and/or the inner coating film 73 may be configured with the coating film 14 described above.

In this medical hollow tube 70, since the outer surface 71a and the inner surface 71b of the hollow tube main body 71 are excellent in the slidability, when the medical hollow tube 70 is brought into contact with another member, the occurrence of the medical hollow tube 70 being stuck can be suppressed, or when a device is inserted into the hollow tube 70, the device can be smoothly inserted therein or removed therefrom.

Further, it is possible to suppress the formation of voids, which are derived from the air bubbles, in the surface of the outer coating film 72 and/or the inner coating film 73 being contiguous to the hollow tube main body 71. As a result, the area where the outer coating film 72 and/or the inner coating film 73 is in contact with the hollow tube main body 71 can be maintained without being reduced, and the high adhesion strength between the outer coating film 72 and/or the inner coating film 73 and the hollow tube main body 71 can be ensured. More specifically, it is possible to allow the adhesion strength to be not lower than 0.30 MPa. It should be noted that the structure of the medical hollow tube 70 can be applied to the hollow tube such as the aforementioned air tube, water tube, or the like for the application use other than the medical application.

EXAMPLES

Next, the present invention will be described in more detail based on examples, but the present invention is not limited to these examples.

Example 1

(Production of Cable)

First, laid 200 coaxial cables each having a diameter of about 0.25 mm were coated with a braided wire to produce a cable core (the cable core 11). Subsequently, a sheath material was extruded at a rate of 5 m/min using an extruder to coat an outer periphery of the cable core, on which was formed a sheath having a thickness of 0.8 mm (cable outer diameter: about 8 mm). A silicone rubber ("KE-541-U" available from Shin-Etsu Chemical Co., Ltd.) was used as the sheath material.

Subsequently, materials to form a coating film (the coating film 14) were compounded. In Example 1, as a rubber component to compose the coating film, an addition reaction type silicone rubber coating agent (trade name: SIL-MARK™, available from Shin-Etsu Chemical Co., Ltd.) was prepared, and as fine particles to compose the coating film, silicone resin fine particles having an average particle diameter of 5 μm (trade name: X-52-1621, available from Shin-Etsu Chemical Co., Ltd.) were prepared. 120 parts by mass of the fine particles, 600 parts by mass of toluene, which acts as a viscosity adjusting solvent, 8 parts by mass of a crosslinking agent (trade name: CAT™, available from Shin-Etsu Chemical Co., Ltd.), and 0.3 parts by mass of a curing catalyst (trade name: CAT-PL-2, available from Shin-Etsu Chemical Co., Ltd.) per 100 parts by mass of the above rubber component were mixed together to compound a coating solution having a proportion of the silicone resin fine particles to the coating film of 55% by mass. Further, 0.1% by mass of hydrophobic fumed silica (trade name: AEROSIL®R972, available from Nippon Aerosil Co., Ltd.) was added to the above coating solution. Note that the silicone resin fine particles content of the above-described coating film was calculated on the assumption that the coating agent was cured with substantially no decrease in mass (with the compounding mass ratio remaining substantially unchanged). Note that the composition of the above coating solution is shown in Table 1 below.

Subsequently, the surface of the sheath provided on the cable core was cleaned. Thereafter, the cable core provided with the sheath was immersed in the above-described coating solution by the dip coating method to form a coating material layer made of the silicone rubber on the surface of the sheath. In the present embodiment, the pulling up speed for the cable core was set at 2 m/min Thereafter, the coating material layer was subjected to a drying and curing treatment at a temperature of 150 degrees C. by heating with a heater (infrared heater) for 10 minutes to form the coating film having irregularities on its surface. The thickness of the resulting coating film was 15 μm.

The above process produced a cable of Example 1.

TABLE 1

| | | | | Example 1 | Example 2 | Example 3 | Example 4 | Comparative example 1 | Comparative example 2 |
|---|---|---|---|---|---|---|---|---|---|
| Coating film | Rubber composition | Rubber component | Addition reaction type silicone rubber | 100 | 100 | 100 | 100 | — | 100 |
| | | | Condensation reaction type silicone rubber | — | — | — | — | 100 | — |
| | | Fine particles | Silicone resin fine particles | 120 | 150 | 120 | 120 | 13 | 120 |
| | | Solvent | Toluene | 600 | 600 | 600 | 600 | — | 600 |
| | | Crosslinking agent | | 8 | 8 | 8 | 8 | — | 8 |
| | | Curing catalyst | | 0.3 | 0.3 | 0.3 | 0.3 | — | 0.3 |
| | | Fumed silica (silica fine particles) | | 0.1 | 0.1 | — | — | — | — |
| | Coating film thickness (μm) | | | 15 | 17 | 15 | 15 | 15 | 15 |
| | Fine particles to coating film proportion (mass %) | | | 55 | 60 | 55 | 55 | 56.5 | 55 |
| | Pull-up speed of cable | | | 2 m/min | 2 m/min | 2 m/min | 2 m/min | 2 m/min | 12 m/min |
| Sheath | Infrared absorber | | | — | — | — | 1 | — | — |
| Evaluation | Coating film surface static friction coefficient (μ) | | | 0.16 | 0.14 | 0.16 | 0.16 | 0.16 | 0.17 |
| | Adhesion strength between sheath and coating film (MPa) | | | 0.40 | 0.32 | 0.39 | 0.44 | 0.22 | 0.40 |
| | Bending resistance | | | ○ | ○ | ○ | ○ | X | ○ |
| | Wiping off resistance | Pre-testing static friction coefficient (μ) | | 0.16 | 0.14 | 0.16 | 0.16 | 0.16 | 0.17 |
| | | Post-testing static friction coefficient (μ) | | 0.17 | 0.15 | 0.19 | 0.18 | 0.45 | 0.30 |
| | | Difference between pre- and post-testing (μ) | | 0.01 | 0.01 | 0.03 | 0.02 | 0.29 | 0.13 |
| | Surface irregularities | No. of fine particles (/1600 μm$^2$) | | 94-96 | 98-101 | 74-79 | 77-81 | 42-52 | 38-58 |
| | | No. of not smaller than 1 μm voids (/1600 μm$^2$) | | None | None | None | None | 40 | None |
| | | No. distribution of fine particles (%) | | 1.05 | 1.51 | 3.27 | 2.53 | 10.6 | 19.6 |

(Parts by mass with no unit of quantity required)

Example 2

In Example 2, a coating solution was compounded and a cable was produced in the same manner as in Example 1 except that the silicone rubber resin particles content was changed from 120 parts by mass to 150 parts by mass, and the proportion of the silicone resin fine particles to the coating film was changed to 60.0% by mass.

Example 3

In Example 3, a coating solution was compounded and a cable was produced in the same manner as in Example 1 except that the fumed silica was not added.

Example 4

In Example 4, a coating solution was compounded and a cable was produced in the same manner as in Example 1 except that $TiO_2$ (the infrared absorber) was added to the sheath material in such a manner that 1 part by mass of the infrared absorber is added per 100 parts by mass of the sheath material.

Comparative Example 1

In Comparative Example 1, a cable was produced using a condensation reaction type silicone rubber coating agent and silicone resin fine particles having an average particle diameter of 5 µm (trade name: X-52-1621, available from Shin-Etsu Chemical Co., Ltd.). Note that, as the coating agent, the condensation reaction type silicone rubber coating agent including a vinyl oxime silane and a solvent (toluene, n-heptane) (trade name: X-93-1755-1, available from Shin-Etsu Chemical Co., Ltd.) was used.

Comparative Example 2

In Comparative Example 2, a coating solution was compounded and a cable was produced in the same manner as in Example 1 except that the pulling up speed of the cable was increased to be 12 m/min.

(Evaluation)

With respect to each cable produced above, the static friction coefficients of the respective coating film and the respective sheath, the adhesion strength between the respective coating film and the respective sheath, the bending resistance when the protective member was attached, the resistance of the respective coating film to being wiped off, and the surface irregularities of the respective coating film were evaluated. Hereinafter, each measurement method will be described.

(Static Friction Coefficient)

First, a cut was made in the length direction in the respective sheath portion with the respective coating film thereon of each cable produced above, and the respective underlying members included in each cable other than the respective sheath with the respective coating film thereon were removed, and the respective sheath with the respective coating film thereon was spread out to produce a respective flat sheet thereof having a length of about 10 cm and a width of about 2.5 cm, and a respective 1.5 cm×1.5 cm square flat sheet thereof. A respective test sheet 1 with the respective flat sheet of the respective sheath with the respective coating film thereon having a length of about 10 cm and a width of about 2.5 cm produced in the above manner and attached to a flat plate, and a respective sheet 2 with the respective 1.5 cm×1.5 cm square flat sheet of the respective sheath with the respective coating film thereon produced in the above manner and attached to a flat plate were produced. The coated surface of the respective sheet 2 was opposed to and brought from above into contact with the coated surface or wiped off coated surface of the respective test sheet 1, and with the flat plate of the respective sheet 2 being acted on by a load W of 2 N from above, the flat plate of the respective sheet 2 was pulled horizontally with a push pull gauge, and the pulling force (frictional force) F for the flat plate of the respective sheet 2 was measured. The static friction coefficient, µ, was calculated from $F=\mu W$. In the present examples, the static friction coefficient was calculated for each of the respective rubber compositions forming the respective coating films and the respective rubber compositions forming the respective sheaths. Note that, herein, the respective sheets 1 and 2 were prepared using the cables after the wiping off testing, and their coefficients of the static friction after the wiping off were measured.

(Adhesion Strength)

Figure 5:
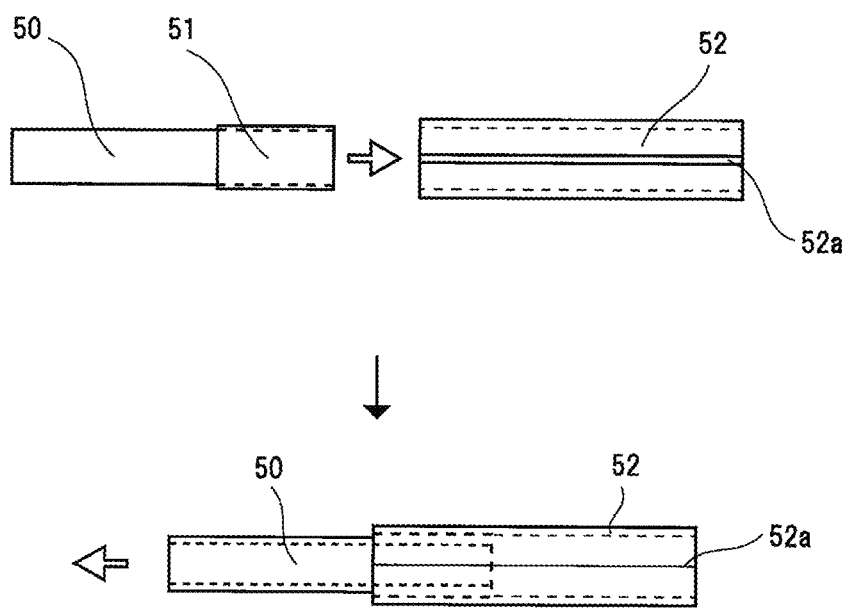
FIG. 5 is a diagram for explaining a method of producing an evaluation sample used for evaluating the adhesion strength between an underlying sheath and an overlying coating film.
Figure 6:
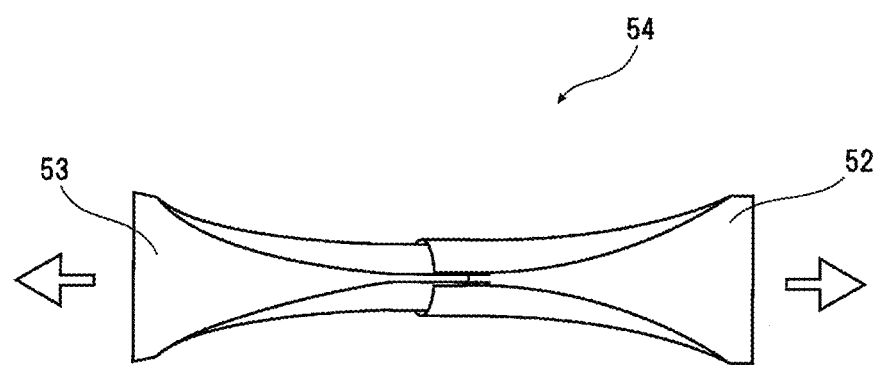
FIG. 6 is a diagram schematically showing a measuring method for measuring the tensile shear strength using the evaluation sample.

The adhesion strength between the underlying sheath and the overlying coating film was measured based on FIGS. 5 and 6. FIG. 5 is a diagram for explaining a method of producing an evaluation sample used for evaluating the adhesion strength between the underlying sheath and the overlying coating film. FIG. 6 is a diagram schematically showing a measuring method for measuring the tensile shear strength using the evaluation sample.

Specifically, first, a respective sample cable having a length of 100 mm was sampled from each cable produced above. Further, a boot material tube 52 (of inner diameter: about 8 mm, thickness: 0.8 mm, length: 100 mm) was prepared, and a cut (a slit) 52a was made in a length direction of that boot material tube. As shown in FIG. 5, an adhesive 51 was applied to an outer peripheral surface of one end of the respective sample cable 50. Subsequently, a portion of the one end of the respective sample cable 50 was wrapped with the boot material tube 52 in such a manner that one section of the cut 52a of the boot material tube 52 is joined to another section, to bond the sample cable 50 and the boot material tube 52 together. Next, the respective underlying members (such as the respective cable core and the like) included in the respective sample cable 50 other than the respective sheath with the respective coating film thereon were pulled and removed to produce a respective sheath material tube 53 with the boot material tube 52 bonded and made integral therewith. Subsequently, a cut was made in the length direction of the respective sheath material tube 53 with the boot material tube 52 bonded and made integral therewith. At this point of time, the cut was made in the respective sheath material tube 53 to be continuous with the cut 52a provided in the boot material tube 52. This resulted in a respective adhesion strength evaluating sample 54 as shown in FIG. 6. Note that the respective sheath material tube 53 and the boot material tube 52 were formed using the same silicone rubbers (static friction coefficient: not lower than 1.0). As the adhesive 51, a commercially available silicone based adhesive KE-45 (available from Shin-Etsu Chemical Co., Ltd.) was used. The bonding region at this point of time was, for example, 10 mm in length×25 mm in outer circumference, and the thickness of the adhesive 51 was on the order of 50 µm to 200 µm. The respective evaluation sample 54 produced in this manner was left to stand in the atmosphere at 25 degrees C. for 168 hours.

The adhesion strength between the respective sheath material tube 53 and the respective coating film was evaluated by measuring the tensile shear strength using the respective evaluation sample 54. Specifically, as shown in FIG. 6, opposite end portions of the sheath material tube 53 and the boot material tube 52 made integral with each other were gripped and pulled at a speed of 500 mm/min, and the tensile shear strength was measured, and the adhesion strength between the sheath material tube 53 and the coating film was measured. Note that the gripping positions for the opposite end portions of the sheath material tube 53 and the boot material tube 52 made integral with each other were adjusted in such a manner that the distance between the gripped opposite end portions of the sheath material tube 53 and the boot material tube 52 made integral with each other was 70 mm. In the present examples, when the adhesion strength was not lower than 0.30 MPa, the adhesion strength was evaluated as the enough adhesion strength.

(Bending Resistance)

The bending resistance was evaluated by bonding a boot to one end of each cable 10 produced above as a protective member with a silicone based adhesive KE-45 to produce a probe cable, repeatedly bending that probe cable and measuring the adhesion strength of that boot to the cable. The sheath and the boot were made of the same silicone rubber ("KE-541-U" available from Shin-Etsu Chemical Co., Ltd.). A bonding area between the probe cable and the boot was 250 mm$^2$ (the size of the bonding region is a longitudinal length of 10 mm and an outer circumferential length of 25 mm).

Figure 7:
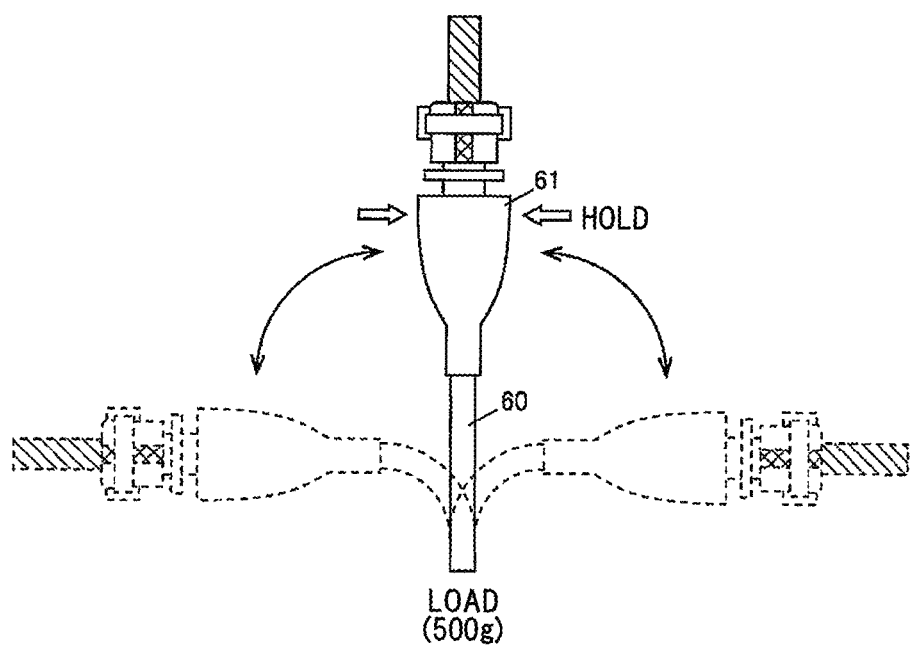
FIG. 7 is a diagram schematically showing a bending resistance testing for the probe cable.

Specifically, the evaluation of the bending resistance was made as shown in FIG. 7. FIG. 7 is a diagram schematically illustrating a bending resistance testing for the probe cable (a length of 1 m). First, a load of 500 g was applied to the probe cable 60, and a part of the boot 61 attached to the end portion of the probe cable 60 was held in such a manner that the probe cable 60 was held in the vertical position, and the operation of bending the held part of the boot 61 to the right by 90 degrees and to the left by 90 degrees alternately at a rate of 30 times/minute was repeatedly performed. Herein, a series of operations of first holding the held part of the boot 61 in the vertical position, then bending it to the left by 90 degrees, again returning it to the vertical position, then bending it to the right by 90 degrees, and again returning it to the vertical position was counted as one time bending operation. The operation of bending the held part of the boot 61 to the right and to the left alternately was repeatedly performed 150,000 times or more in total. In the present examples, when no peeling or fracture of the boot 61 occurred in the above bending resistance testing, the bending resistance was determined as good (○), or when a peeling or fracture of the boot 61 occurred in the above bending resistance testing, the bending resistance was determined as poor (×).

(Wiping Off Resistance)

Figure 8A:
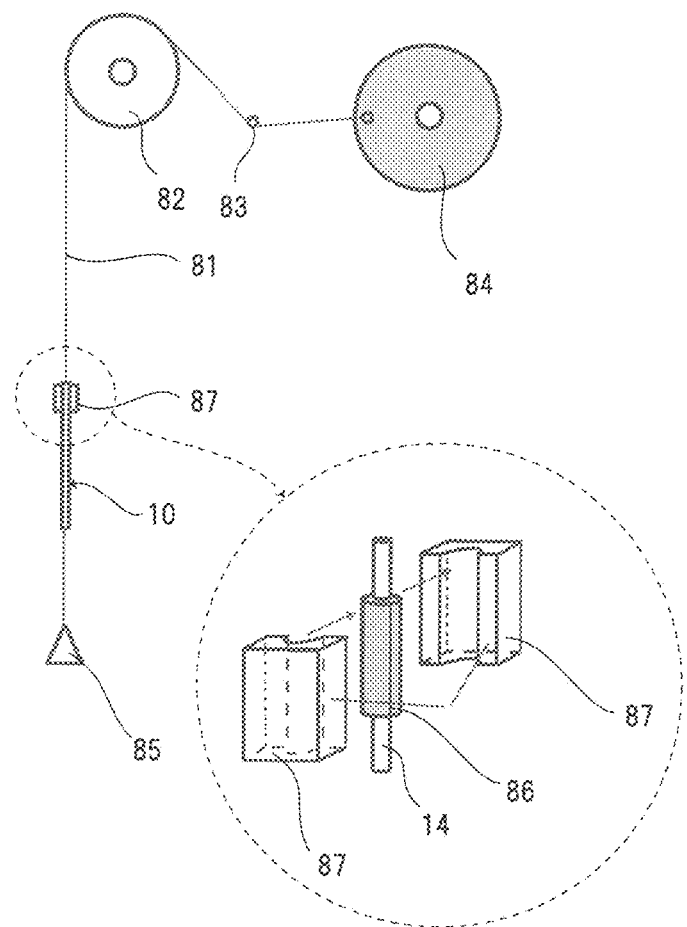
FIG. 8A is a diagram for explaining a wiping off testing method.
Figure 8B:
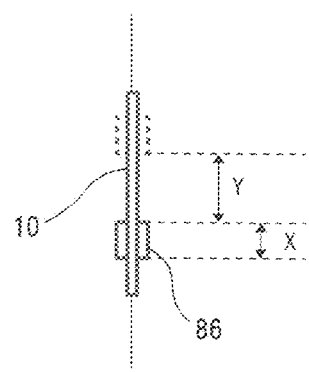
FIG. 8B is a diagram for explaining a wiping direction length of a cotton cloth and a wiping off length by moving the cotton cloth.

The resistance of the coating film 14 to being wiped off was evaluated by a testing shown in FIGS. 8A and 8B repeatedly wiping off the surface of the coating film 14 with a cotton cloth impregnated with a disinfecting alcohol. FIG. 8A is a diagram for explaining the wiping off testing method. FIG. 8B is a diagram for explaining a wiping direction length of the cotton cloth and a wiping off length by moving the cotton cloth. Specifically, first, as shown in FIG. 8A, a string 81 was tied to one end of the cable 10 (length 10 m), and the string 81 was passed around a pulley 82 and a guide pulley 83, and was joined to a rotatable rotating circular plate 84. The cable 10 was hung and a weight 85 of 400 g was tied to a lower end portion of the cable 10. This allowed the cable 10 to be held to be able to be reciprocated upward and downward in the vertical direction by the rotation of the rotating circular plate 84. Then, a cotton-like gauze cloth (length 50 mm along the wiping direction of the cotton cloth) was wrapped around the surface of the coating film 14 of the cable 10 as a cotton cloth 86. The cotton cloth 86 was pre-impregnated with a disinfecting ethanol (including 75% to 80% ethanol). Subsequently, the wrapped cotton cloth 86 was held to be covered with wiper holders 87 and 87 made of a silicone rubber sponge (hereinafter also referred to as "holders 87"), and the holders 87 were adjusted in such a manner that the cotton cloth 86 is brought contiguous to the surface of the coating film 14 at a shearing stress of $2\times10^{-3}$ MPa to $4\times10^{-3}$ MPa. Subsequently, by reciprocating the cable 10 upward and downward relative to the holders 87, the surface of the coating film 14 of the cable 10 was wiped off with the cotton cloth 86 held in the holders 87. In the present examples, as shown in FIG. 8B, the wiping direction length X of the cotton cloth 86 was set at 50 mm, the wiping off length Y (moving distance Y) of the cable 10 by the cotton cloth 86 was set at 150 mm, and a one-way moving distance of the cotton cloth 86 was set at 200 mm. Further, the cable 10 was reciprocated 40 to 60 times per minute, and the wiping off speed for the surface of the coating film 14 was set at a speed of 80 times/min to 120 times/min (40 cycles/min to 60 cycles/min). Also, every time the cable 10 was reciprocated 500 times relative to the cotton cloth 86, the cotton cloth 86 was replaced with a new one. In the present examples, the static friction coefficient on the surface of the coating film 14 after 20,000 wiping off operations (10,000 reciprocations) was measured, and the difference (the absolute value of the difference) between the static friction coefficients of the coating film 14 before and after the testing, (<static friction coefficient after the testing>-<static friction coefficient before the testing>), was calculated. When the difference (the absolute value of the difference) between the static friction coefficients of the coating film 14 before and after the testing was not greater than 0.1, the cable 10 was evaluated as having less damage to the coating film 14 due to the wiping off, and was evaluated as excellent in the resistance of the coating film 14 to being wiped off. Note that the environmental temperature was set at 25±3 degrees C., and the environmental humidity was 50±10%.

As the cotton cloth 86, "BEMCOT regular type (M-3II), size 250 mm×250 mm, quarter-fold type" available from Asahi Kasei Corporation, which is a long fiber non-woven fabric including cotton linters, was used. A single BEMCOT (folded in four) was unfolded and a piece with a size of 50 mm×175 mm was cut out from the cloth with a size of 250 mm×250 mm The cut piece of BEMCOT was entirely and uniformly impregnated with the disinfecting alcohol (approximately 2.5 ml) dropped from a dropper. Next, the cut piece of BEMCOT impregnated with the disinfecting alcohol was wrapped around the cable 10 (by approximately 7 cycles) in such a manner that a long side of the cut piece of BEMCOT coincides with a circumferential direction of the cable 10. Here, the long side length of the cut piece of BEMCOT was adjusted based on an outer diameter of the cable 10 in order to wind the cut piece of BEMCOT around the cable 10 by approximately 7 cycles.

Further, in the wiping off testing, after the cotton cloth 86 has been reciprocated 250 times, 2.5 ml of the disinfecting alcohol was supplied as liquid droplet to the cotton cloth 86, for maintaining the impregnation status of the cotton cloth 86 with the alcohol. This liquid droplet was made by dropping the disinfecting alcohol by the dropper on an upper end of the cotton cloth 86 held by the holders 87 along the circumferential direction of the cable 10 such that the cotton cloth 86 is impregnated with the disinfecting alcohol. Note that the additive amount of the disinfecting alcohol may be determined in order not to dry the cotton cloth due to volatilization at the time of reciprocating the cotton cloth 86 for 250 times in the wiping off testing. In the present Examples, the additive amount was adjusted to be 2.5 ml.

Further, a force to bring the cotton cloth 86 contiguous to the cable 10 (the shearing stress) was adjusted as follows. The cotton cloth 86 prepared by the above method was wrapped around the cable 10 and held to be covered with wiper holders 87 and 87. Next, one end of the cable 10 held by the holders 87 was pulled horizontally by a push pull gauge (push pull scale), and the shearing stress obtained by dividing a force when the cable 10 started to move with respect to the holders 87 by a surface area of the cable 10 covered by the wiper holders 87, 87 was adjusted to be within a range of $2 \times 10^{-3}$ MPa to $4 \times 10^{-3}$ MPa. Each of the holders 87 was made of the silicone rubber sponge and provided with a recess at a portion contacting the cable 10 wrapped with the cotton cloth 86. The recesses of the holders 87, 87 were processed to have a cylindrical shape when the holders 87, 87 are combined with each other. In the case where the shearing stress was out the predetermined range, the holding force (clamping force) of the wiper holders 87, 87 was adjusted by changing the size (diameter) of the recesses of the wiper holders 87, 87 (parts for holding the cable 10). Note that the shearing stress was adjusted each time when the cotton cloth 86 was changed.

The weight 85 is a driving source for moving the cable 10 downwardly (free fall) and may be weighted in such a manner that a time required for moving the cotton cloth 86 downwardly for 200 mm would be 0.67 sec/cycle to 1 sec/cycle (40 cycles/min to 60 cycles/min). Here, at the time of adjusting the shearing stress, the weight 85 was set in such a manner that the gravity to the weight 85 would be 1.5 times to 2 times of the force when the cable 10 starts to move with respect to the wiper holders 87, 87 (the product of the shearing stress by the surface area of the cable 10 covered by the wiper holders 87, 87).

(Surface Irregularities)

The surface irregularities of the coating films were evaluated by observing the surfaces of the coating films with an electron microscope, and counting the number of fine particles and the number of voids present per unit area, and calculating the number distribution of the fine particles.

The number of the fine particles and the number of the voids per unit area were calculated by observing the surfaces of the coating films with the electron microscope.

For the number distribution of the fine particles, first, an image of the surface of each of the coating films was photographically recorded at a magnification of 1000 times, and four regions of 40 μm×40 μm on the surface of each of the coating films were optionally selected, the numbers of the fine particles present in each of the four regions were counted, and the number of the fine particles per unit area was calculated. And when, of the numbers of the fine particles present in each of the four regions, the maximum value was denoted by $N_{max}$ and the minimum value was denoted by $N_{min}$, the number distribution, which was calculated from the formula $((N_{max}-N_{min})/(N_{max}+N_{min}))\times 100$, was calculated. In the present examples, when the calculated numerical value for the number distribution of the fine particles was not more than 5%, the variation in the number of the fine particles was evaluated as small.

(Evaluation Results)

Table 1 summarizes the evaluation results. As shown in Table 1, in Examples 1 to 4, the static friction coefficients of their respective coating films were 0.5 or less, and it was confirmed that their respective coating films were excellent in the slidability. Further, in Examples 1 to 4, since the strengths of the adhesion between their respective coating films and their respective sheaths were not lower than 0.3 MPa, and no peeling of the boot occurred even in the bending testing, it was confirmed that the strengths of the adhesion of their respective coating films were high.

Also, in Examples 1 to 4, regarding the resistance of their respective coating films to being wiped off, even after their respective coating films were repeatedly wiped off, the static friction coefficients of their respective coating films were not varied significantly as compared to those calculated before the testing, so it was confirmed that the differences between the static friction coefficients of their respective coating films before and after the testing were not greater than 0.1.

Figure 9:
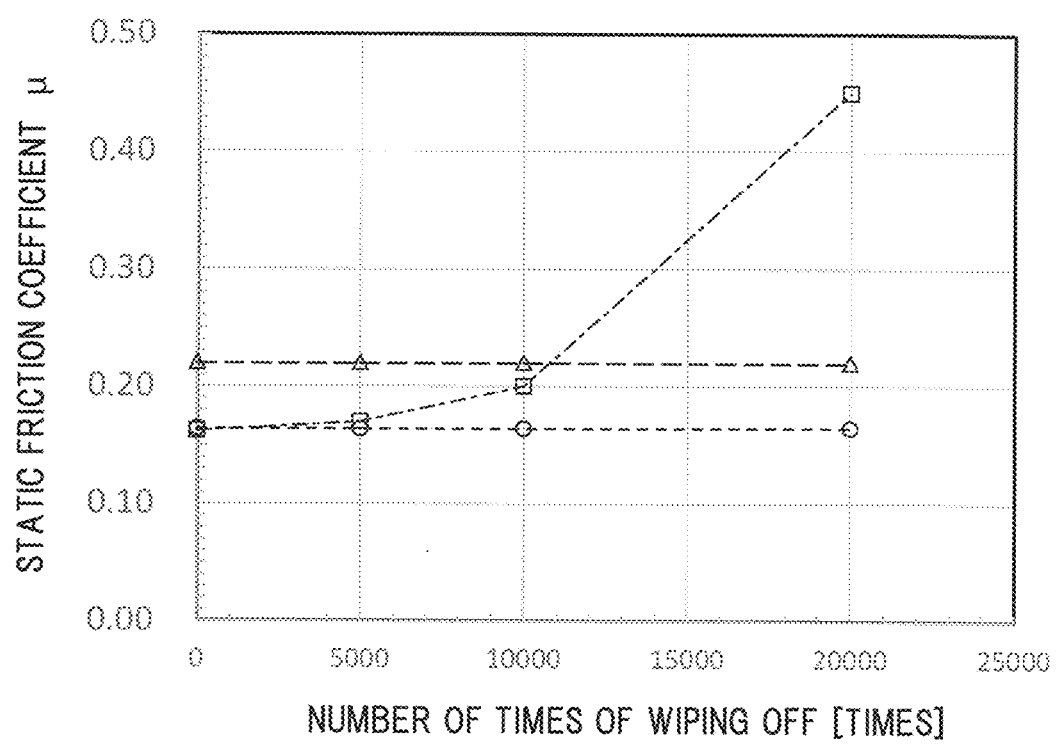
FIG. 9 is a diagram showing a change in the static friction coefficient of the coating film according to the number of times of wiping off.

Here, the change in the static friction coefficient of the coating film of Example 1 due to the wiping off operations will be specifically described with reference to FIG. 9. FIG. 9 is a diagram showing the changes in the static friction coefficients of the coating films according to the number of times of wiping off, where the horizontal axis represents the number of times of wiping off [times], and the vertical axis represents the static friction coefficient of the coating films. In FIG. 9, regarding the changes in the static friction coefficients of the coating films, Example 1 was indicated by circular (○) plotting, Example 1 (○), Example 2 was indicated by a square (□) plotting, and Example 3 was indicated by a triangle (△) plotting, while Comparative Example 1 was indicated by a diamond (◇) plotting, and Comparative Example 2 was indicated by a cross (×) plotting, and as a reference example, the static friction coefficients of a coating film made of a polyvinyl chloride (PVC) was indicated by asterisk (*) plotting. As shown in FIG. 9, the static friction coefficient of the coating film of Example 1 was 0.16 before the wiping off testing, and was 0.17 after the coating film of Example 1 was wiped off 20,000 times, thus it was confirmed that the difference (the absolute value of the difference) between the static friction coefficients of the coating film of Example 1 before and after the testing was 0.01. Further, the static friction coefficient of the coating film of Example 2 was 0.14 before the wiping off testing, and was 0.15 after the coating film of Example 2 was wiped off 20,000 times, and thus it was confirmed that the difference (the absolute value of the difference) between the static friction coefficients of the coating film of Example 2 before and after the testing was 0.01. The static friction coefficient of the coating film of Example 3 was 0.16 before the wiping off testing, and was 0.19 after the coating film of Example 3 was wiped off 20,000 times, thus it was confirmed that the difference (the absolute value of the difference) between the static friction coefficients of the coating film of Example 3 before and after the testing was 0.03. The static friction coefficient of the coating film of Example 4 was 0.16 before the wiping off testing, and was 0.18 after the coating film of Example 4 was wiped off 20,000 times, thus it was confirmed that the difference (the absolute value of the difference) between the static friction coefficients of the coating film of Example 4 before and after the testing was 0.02. That is, it was confirmed that, in Examples 1 to 4, even after their respective coating films were wiped off 20,000 times, the static friction coefficients of their respective coating films were not greatly varied, so their respective coating films were able to be kept high in the slidability, and were excellent in the resistance to being wiped off. In addition, it was confirmed that the static friction coefficients of the respective coating films of Examples 1 to 4 were able to be kept lower than that of the PVC coating film.

On the other hand, in Comparative Example 1, it was confirmed that, although the coating film was excellent in the slidability, not only the adhesion strength between the sheath and the coating film was low but also the resistance of the coating film to being wiped off was low. Specifically, in Comparative Example 1, the adhesion strength between the sheath and the coating film was 0.22 MPa, and the boot was peeled off by the bending testing. As indicated by the square (◇) plotting in FIG. 9, the static friction coefficient of the coating film of Comparative Example 1 was 0.16 before the wiping off testing, and was 0.45 after the coating film of Comparative Example 1 was wiped off 20,000 times, thus the difference (the absolute value of the difference) between the static friction coefficients of the coating film of Comparative Example 1 before and after the testing was 0.29. In Comparative Example 1, the static friction coefficient of the coating film was gradually increased by repeating the wiping off, and the slidability of the coating film was not able to be maintained. That is, it was confirmed that the coating film of Comparative Example 1 was poor in the resistance to being wiped off.

In Comparative Example 2, it was confirmed that, although the coating film was excellent in the slidability and the adhesion strength between the sheath and the coating film but also the resistance of the coating film to being wiped off was lower than Examples 1 to 3. As indicated by the cross (×) plotting in FIG. 9, the static friction coefficient of the coating film of Comparative Example 2 was 0.17 before the wiping off testing, and was 0.30 after the coating film of Comparative Example 2 was wiped off 20,000 times, thus the difference (the absolute value of the difference) between the static friction coefficients of the coating film of Comparative Example 2 before and after the testing was 0.13. In Comparative Example 2, the static friction coefficient of the coating film was gradually increased by repeating the wiping off, and the slidability of the coating film was not able to be maintained. That is, it was confirmed that the coating film of Comparative Example 2 was poor in the resistance to being wiped off in comparison with Examples 1 to 3.

This difference in the properties is due to the distribution of the fine particles on the surface of the coating film and the resulting surface irregularities shape. Hereinafter, these points will be described.

Figure 10A:
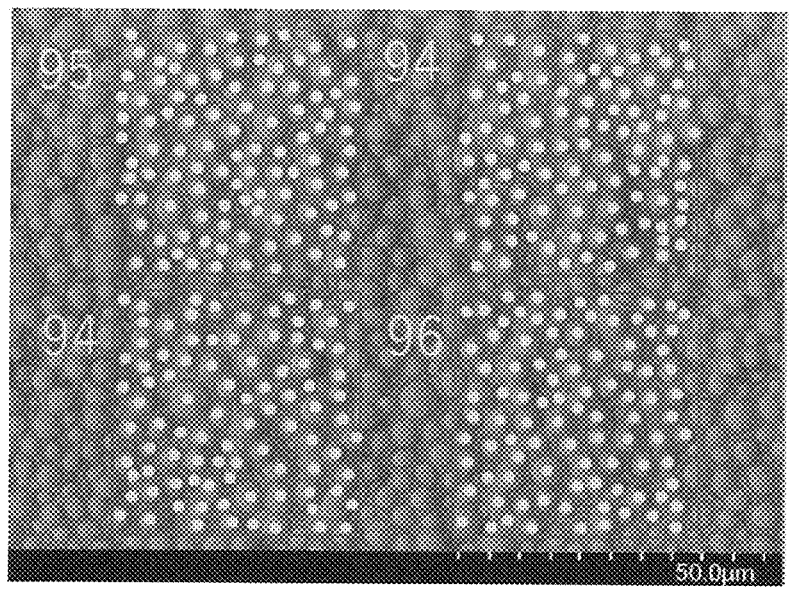
FIG. 10A is an SEM image showing a coating film surface of a cable of Example 1.
Figure 10B:
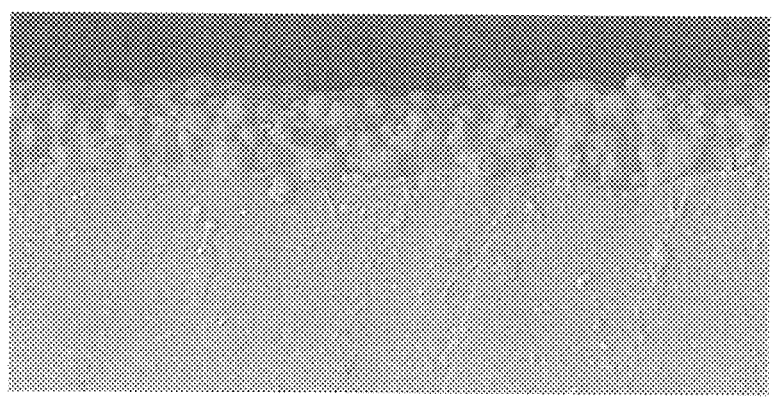
FIG. 10B is an SEM image showing a cross section of the coating film of the cable of Example 1.
Figure 11A:
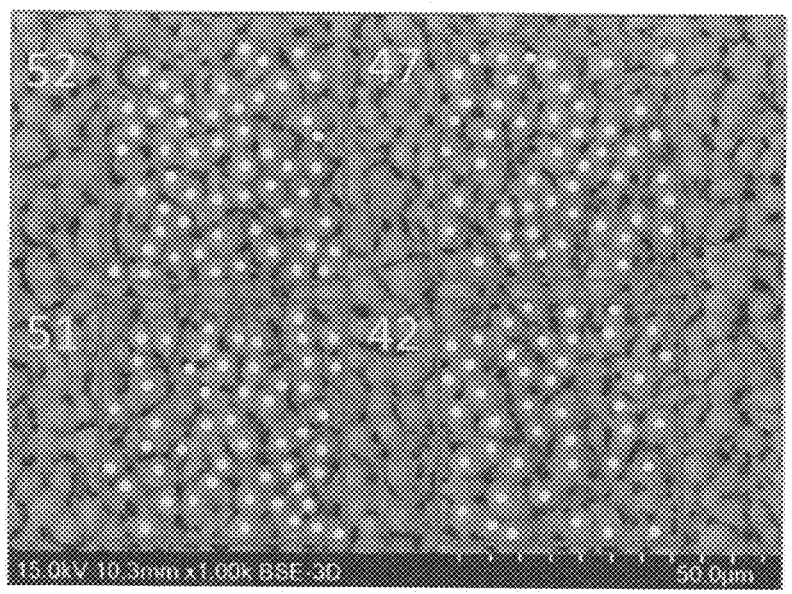
FIG. 11A is an SEM image showing a coating film surface of a cable of Comparative Example 1.
Figure 11B:
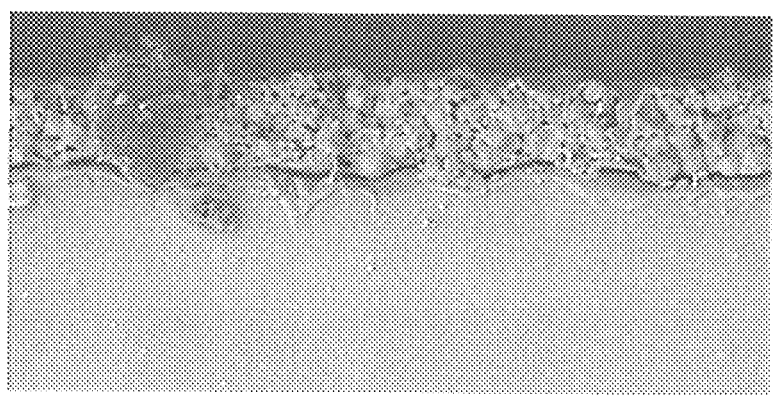
FIG. 11B is an SEM image showing a cross section of the coating film of the cable of Comparative Example 1.
Figure 12:
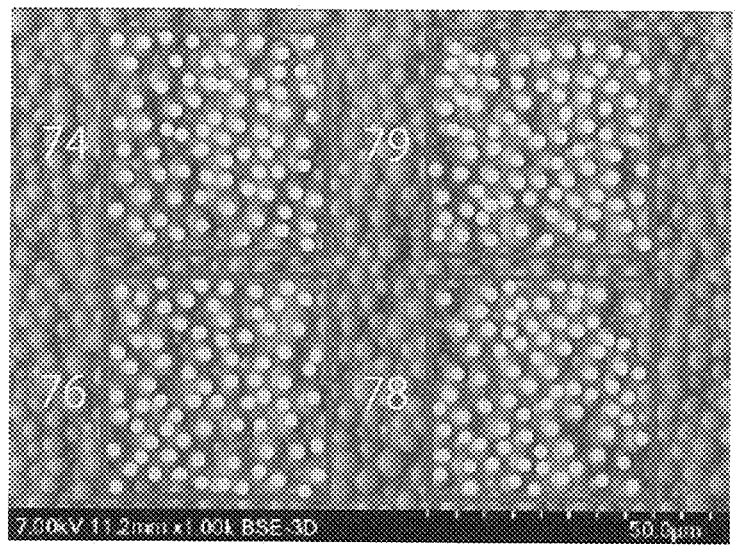
FIG. 12 is an SEM image showing a cross section of the coating film of the cable of Example 3.
Figure 13:
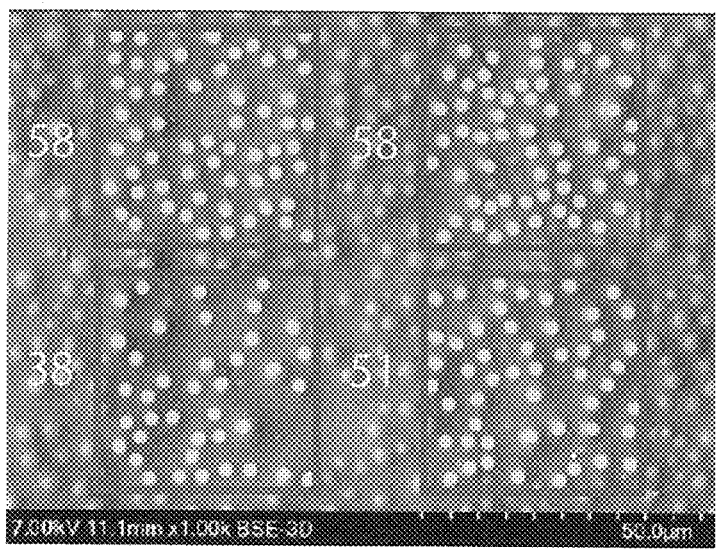
FIG. 13 is an SEM image showing a cross section of the coating film of the cable of Comparative Example 2.

For each of the Examples 1 to 4 and Comparative Examples 1 and 2, the surface irregularities and cross section of the coating film before the wiping off testing were checked, and as a result, it was observed that the surfaces of the coating films of the Examples 1 to 4 and Comparative Examples 1 and 2 were in states as shown in FIGS. 10A, 10B, 11A, 11B, 12 and 13 respectively. FIG. 10A is an SEM image showing the surface of the coating film of Example 1. FIG. 10B is an SEM image showing the cross section of the coating film of Example 1. FIG. 11A is an SEM image showing the surface of the coating film of Comparative Example 1. FIG. 11B is an SEM image showing the cross section of the coating film of Comparative Example 1. FIG. 12 is an SEM image showing a cross section of the coating film of the cable of Example 3. FIG. 13 is an SEM image showing a coating film surface of a cable of Comparative Example 2. Comparing these figures, it was observed that, in the coating film of Example 1, the fine particles were densely distributed, whereas, in Comparative Example 1 and Comparative Example 2, not only the fine particles but also the collapse formations (the portions shown in black in FIGS. 11A and 11B) were present. In addition, it was observed that, in the coating film of Comparative Example 1, the air bubbles (voids) were present over a wide range on the surface of the coating film being contiguous to the sheath, whereas, in the coating film of Example 1, the air bubbles (voids) were reduced as compared with Comparative Example 1. In Comparative Example 2, the air bubbles were not observed but the number of the fine particles existing at the surface were low and the distribution thereof was sparse.

As a result of counting the number of the fine particles based on the SEM image, the number of the fine particles in Example 1 was 94 to 96 per 1600 $\mu m^2$ area (40 $\mu m$ square), the number of the fine particles in Example 2 was 98 to 101 per 1600 $\mu m^2$ area (40 $\mu m$ square), the number of the fine particles in Example 3 was 74 to 79 per 1600 $\mu m^2$ area (40 $\mu m$ square), and the number of the fine particles in Example 4 was 77 to 81 per 1600 $\mu m^2$ area (40 $\mu m$ square), whereas the number of the fine particles in Comparative Example 1 was 42 to 52 per 1600 $\mu m^2$ area (40 pm square), and the number of the fine particles in Comparative Example 2 was 38 to 58 per 1600 $\mu m^2$ area (40 $\mu m$ square). That is, Examples 1 to 4 were larger in the number of the distributed fine particles than Comparative Examples 1 and 2. Further, in Examples 1 to 4, substantially no void having a size of not smaller than 1 $\mu m$ was present, whereas in Comparative Example 1, at least 40 voids having a size of not smaller than 1 $\mu m$ were present within the range of 40 $\mu m$ square. Further, as a result of calculating the number distribution of the fine particles from the number of the fine particles in each region, the number distribution of the fine particles was 1.05% in Example 1, 1.51% in Example 2, 3.27% in Example 3, and 2.53% in Example 4, so the variation in the number distribution of the fine particles was small, namely, not larger than 5% in all the Example 1 to 4. On the other hand, the number distribution of the fine particles was 10.6% in Comparative Example 1, and 19.6% in Comparative Example 2, so the distribution of the fine particles in the coating film was not uniform, and the variation in the number distribution of the fine particles was large.

Figure 14:
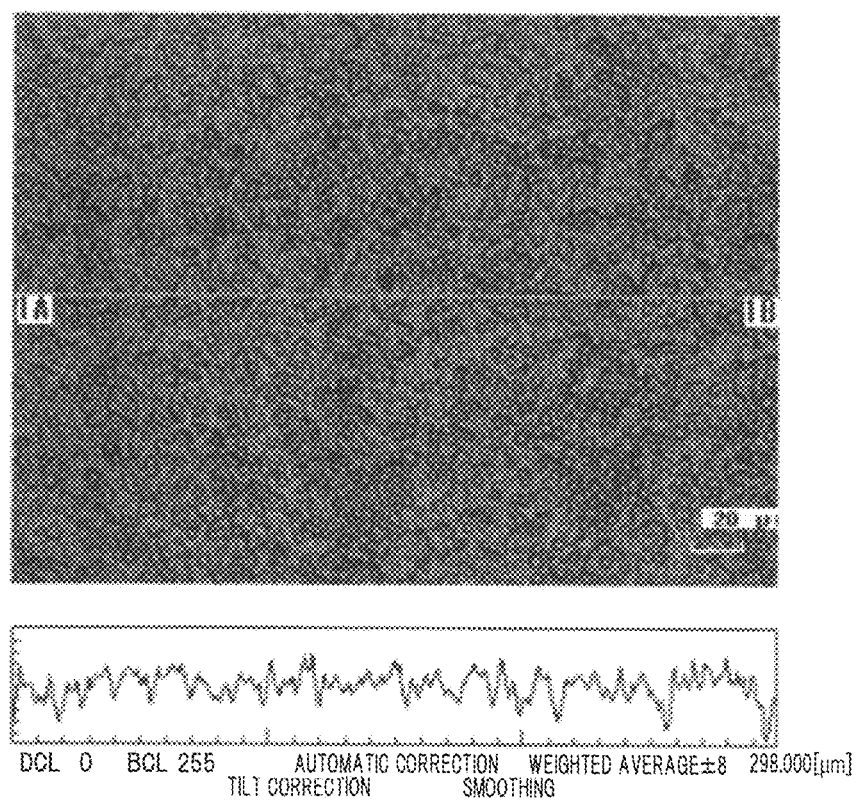
FIG. 14 is a diagram showing a surface profile of the coating film of Example 1.
Figure 15:
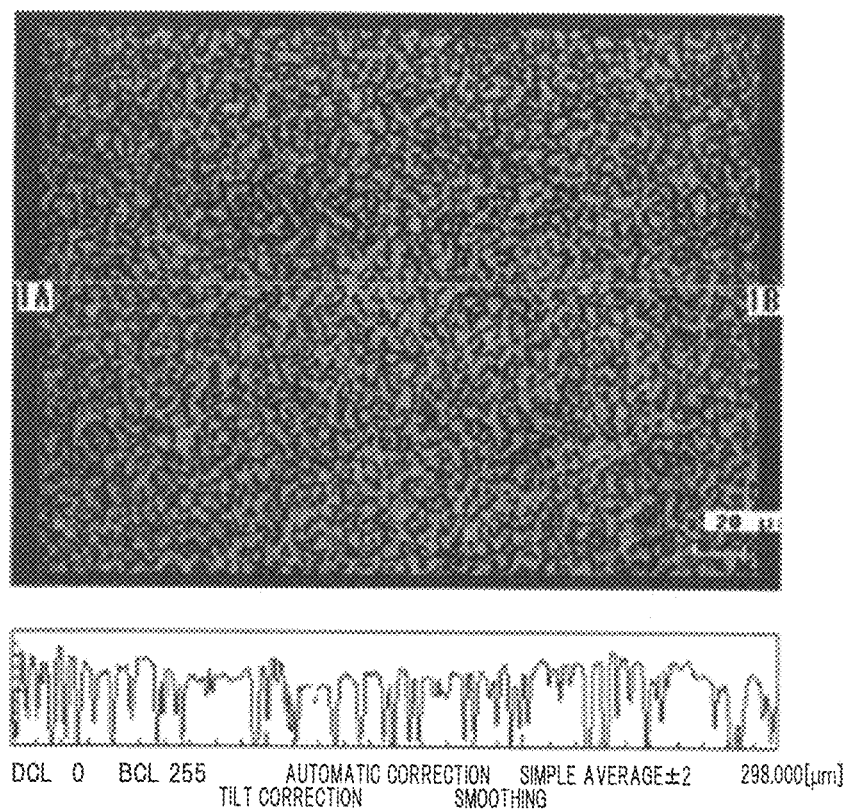
FIG. 15 is a diagram showing a surface profile of the coating film of Comparative Example 1.

Furthermore, as a result of obtaining the surface profiles for the respective coating films of Example 1 and Comparative Example 1, results as shown in FIGS. 14 and 15 were obtained. FIG. 14 is a diagram showing the surface profile for the coating film of Example 1. FIG. 15 is a diagram showing the surface profile for the coating film of Comparative Example 1. As shown in FIG. 14, in the coating film of Example 1, no collapse formation due to void formation was observed, so it was confirmed that the projecting portions formed by the fine particles were present in larger quantity than the quantity of the collapsed portion due to the collapse formation. On the other hand, in Comparative Example 1, as shown in FIG. 15, it was confirmed that the collapsed portions due to the collapse formations were present in large quantity on the surface of the coating film.

The collapses formed in the coating film were caused by the air bubbles formed as a result of a condensation reaction when the condensation reaction type silicone rubber was cured. When the coating film was wiped off with the cotton cloth, the above collapses formed in the coating film caused the cotton cloth to be easily stuck at the edges of the collapses, and therefore the coating film was easily damaged by being wiped off with the cotton cloth. As a result, in Comparative Example 1, the fine particles in the coating film were considered to fall off by the coating film being wiped off, thereby tending to increase the static friction coefficient of the coating film, and failing to maintain the slidability of the coating film over a long period of time. Further, the presence of the voids in the contact surface of the coating film with the underlying sheath was also considered to reduce the contact area between the coating film and the underlying sheath, and thereby lower the adhesion strength therebetween.

In this regard, in the present examples, the use of the addition reaction type silicone rubber allowed suppressing the formation of the air bubbles resulting from the curing of the addition reaction type silicone rubber, and thereby reducing the collapse formation on the surface of the coating film and the void formation in the coating film. In addition, preferably, the self-ordering of the fine particles was promoted by adjusting the pulling up speed for the cable when applying the coating material by the dipping method. According to Example 1 and Comparative Example 2, it was found that the distribution variation of the fine particles in the coating film largely changes depending on the pulling up speed for the cable. In Comparative Example 2, the pulling up speed for the cable was excessively increased so that the self-ordering of the fine particles was not promoted and the number of the fine particles was 38 to 58 per unit area, namely, the distribution of the fine particles was sparse in comparison with Example 1 (94 to 96 per unit area). Further, it was confirmed that the number distribution of the fine particles was 19.6%, so that the distribution variation is larger than 1.05% in Example 1. As a result, it is assumed that the static friction coefficient of the coating film tends to be increased due to the falling out of the fine particles or the like by the wiping off so that the slidability was not maintained in Comparative Example 2.

Further, according to Examples 1 and 3, the fine particles can be distributed more densely at the surface of the coating film by adding the fumed silica to the rubber composition. As a result, it is possible to achieve the coating film which is more excellent in the slidability, the adhesion strength between the coating film and the sheath, and the resistance to being wiped off.

As a result of comparison between Example 3 and Example 4, it was confirmed that the adhesion strength between the coating film and the sheath can be increased by compounding the infrared absorber as in Example 4 more than Example 3 in which the infrared absorber was not compounded.

<Preferred Aspects of the Present Invention>

Hereinafter, preferred aspects of the present invention will be described.

(Supplementary Description 1)

According to one embodiment of the present invention, aspect of the present invention, there is provided a cable, comprising: a sheath; and a coating film covering a circumference of the sheath, the coating film adhering to the sheath, wherein the coating film comprises a rubber composition including a rubber component and fine particles, with a static friction coefficient on a surface of the coating film being 0.5 or less, wherein the coating film comprises a resistance to being wiped off in such a manner that, when the coating film is subjected to a testing such that a long fiber non-woven fabric including cotton linters including an alcohol for disinfection with a length of 50 mm along a wiping direction is brought contiguous to the surface of the coating film at a shearing stress of $2 \times 10^{-3}$ MPa to $4 \times 10^{-3}$ MPa, followed by wiping off the surface of the coating film at a speed of 80 times/min to 120 times/min and 20,000 repetitions thereof for a wiping direction length of 150 mm, a difference (an absolute value of a difference) between the static friction coefficients of the coating film before and after the testing is not greater than 0.1.

(Supplementary Description 2)

In the aspect of supplementary description 1 above, an adhesion strength between the sheath and the coating film is 0.30 MPa or more.

(Supplementary Description 3)

In the aspect of supplementary description 1 or 2 above, the rubber component is at least one of a silicone rubber and a chloroprene rubber.

(Supplementary Description 4)

In the aspects of supplementary descriptions 1 to 3 above, the rubber component is a silicone rubber, while the fine particles include at least any one of silicone resin fine particles, silicone rubber fine particles, and silica fine particles.

(Supplementary Description 5)

In the aspects of supplementary descriptions 1 to 4 above, the fine particles have a higher hardness than that of the rubber component.

(Supplementary Description 6)

In the aspects of supplementary descriptions 1 to 5 above, the fine particles comprise an average particle diameter of 1 μm or more and 10 μm or less.

(Supplementary Description 7)

In the aspects of supplementary descriptions 1 to 6 above, the coating film comprises a thickness of 3 pm or more and 100 μm or less.

(Supplementary Description 8)

In the aspects of supplementary descriptions 1 to 7 above, the sheath comprises a silicone rubber.

(Supplementary Description 9)

In the aspects of supplementary descriptions 1 to 6 above, the rubber component is an addition reaction type silicone rubber.

(Supplementary Description 10)

In the aspects of supplementary descriptions 1 to 9 above, when the number of the fine particles per unit area is measured in any plurality of parts of the surface of the coating film, a number distribution, which is calculated from a formula $(N_{max}-N_{min})/(N_{max}+N_{min}) \times 100$ where $N_{max}$ is a maximum value of the number of the fine particles per unit area and $N_{min}$ is a minimum value of the number of the fine particles per unit area, is not more than 5%.

(Supplementary Description 11)

In the aspects of supplementary descriptions 1 to 10 above, in the surface of the coating film, the number of voids comprising a size of not smaller than 1 μm present per unit area is not more than 5/40 μm square.

(Supplementary Description 12)

In the aspects of supplementary descriptions 1 to 11 above, a quantity of the fine particles in the rubber composition is not lower than 10% by mass and not higher than 60% by mass to a total of the rubber component and the fine particles.

(Supplementary Description 13)

In the aspects of supplementary descriptions 1 to 12 above, the cable is configured to be connectable to a medical device.

(Supplementary Description 14)

In the aspects of supplementary descriptions 1 to 13 above, the sheath further comprises an infrared absorber.

(Supplementary Description 15)

In the aspects of supplementary description 14 above, a content of the infrared absorber is 0.1% by mass to 10% by mass per 100 parts by mass of a material of the sheath.

(Supplementary Description 16)
In the aspects of supplementary description 14 or 15 above, the infrared absorber comprises titanium oxide.

(Supplementary Description 17)
According to another aspect of the present invention, there is provided a medical hollow tube or a hollow tube, comprising: a hollow tube main body including an inner surface and an outer surface; and a coating film covering at least one of the inner surface and the outer surface of the hollow tube main body, the coating film adhering to the hollow tube main body, wherein the coating film comprises a rubber composition including a rubber component and fine particles, with a static friction coefficient on a surface of the coating film being 0.5 or less, wherein the coating film comprises a resistance to being wiped off in such a manner that, when the coating film is subjected to a testing such that a long fiber non-woven fabric including cotton linters including an alcohol for disinfection with a length of 50 mm along a wiping direction is brought contiguous to the surface of the coating film at a shearing stress of $2 \times 10^{-3}$ MPa to $4 \times 10^{-3}$ MPa, followed by wiping off the surface of the coating film at a speed of 80 times/min to 120 times/min and 20,000 repetitions thereof for a wiping direction length of 150 mm, a difference (an absolute value of a difference) between the static friction coefficients of the coating film before and after the testing is not greater than 0.1.

(Supplementary Description 18)
In the aspects of supplementary description 17 above, the hollow tube main body further comprises an infrared absorber.

(Supplementary Description 19)
In the aspects of supplementary description 18 above, a content of the infrared absorber is 0.1% by mass to 10% by mass per 100 parts by mass of a material of the hollow tube main body.

(Supplementary Description 20)
In the aspects of supplementary description 18 or 19 above, the infrared absorber comprises titanium oxide.

(Supplementary Description 21)
According to another aspect of the present invention, there is provided a molded article, comprising: a molded article main body; and a coating film covering a surface of the molded article main body, the coating film adhering to the molded article main body, wherein the coating film comprises a rubber composition including a rubber component and fine particles, with a static friction coefficient on a surface of the coating film being 0.5 or less, wherein the coating film comprises a resistance to being wiped off in such a manner that, when the coating film is subjected to a testing such that a long fiber non-woven fabric including cotton linters including an alcohol for disinfection with a length of 50 mm along a wiping direction is brought contiguous to the surface of the coating film at a shearing stress of $2 \times 10^{-3}$ MPa to $4 \times 10^{-3}$ MPa, followed by wiping off the surface of the coating film at a speed of 80 times/min to 120 times/min and 20,000 repetitions thereof for a wiping direction length of 150 mm, a difference (an absolute value of a difference) between the static friction coefficients of the coating film before and after the testing is not greater than 0.1.

(Supplementary Description 22)
In the aspects of supplementary description 21 above, the molded article main body further comprises an infrared absorber.

(Supplementary Description 23)
In the aspects of supplementary description 22 above, a content of the infrared absorber is 0.1% by mass to 10% by mass per 100 parts by mass of a material of the molded article main body.

(Supplementary Description 24)
In the aspects of supplementary description 22 or 23 above, the infrared absorber comprises titanium oxide.

Although the invention has been described with respect to the specific embodiments for complete and clear disclosure, the appended claims are not to be thus limited but are to be construed as embodying all modifications and alternative constructions that may occur to one skilled in the art which fairly fall within the basic teaching herein set forth.

What is claimed is:
1. A cable, comprising:
   a sheath; and
   a coating film covering around the sheath, the coating film adhering to the sheath,
   wherein the sheath comprises an infra-red absorbing component comprising at least one of a titanium oxide and a carbon and the coating film comprises a rubber composition including a thermal curing rubber component,
   wherein a static friction coefficient on a surface of the coating film is 0.5 or less,
   wherein the sheath and the coating film are heated by infra-red light which is absorbed by the infra-red absorbing component to suppress uneven curing in the coating film such that an adhesion strength between the sheath and the coating film is about 0.44 MPa or more, and
   wherein a content of the at least one of titanium oxide and carbon is 1.0% by mass to 10% by mass per 100 parts by mass of a material of the sheath.

2. The cable according to claim 1, wherein the thermal curing rubber component is an addition reaction type silicone rubber.

3. The cable according to claim 1, wherein the sheath comprises a silicone rubber.

4. The cable according to claim 1, wherein no voids having a size of 10 µm or more are substantially present in the surface of the coating film when observed with an electron microscope SEM in a condition of a magnification of 1000 times.

5. A medical hollow tube, comprising:
   a hollow tube main body; and
   a coating film covering at least one of an inner surface and an outer surface of the hollow tube main body, the coating film adhering to the hollow tube main body,
   wherein the hollow tube main body comprises at least one of a titanium oxide and a carbon and the coating film comprises a rubber composition including a thermal curing rubber component,
   wherein a static friction coefficient on a surface of the coating film is 0.5 or less, and
   wherein the sheath and the coating film are heated by infra-red light which is absorbed by the infra-red absorbing component to suppress uneven curing in the coating film such that an adhesion strength between the hollow tube main body and the coating film is about 0.44 MPa or more, and
   wherein a content of the at least one of titanium oxide and carbon is 1.0% by mass to 10% by mass per 100 parts by mass of a material of the sheath.

6. A molded article, comprising:

a molded article main body; and a coating film covering a surface of the molded article main body, the coating film adhering to the molded article main body, wherein the molded article main body comprises at least one of a titanium oxide and a carbon and the coating film comprises a rubber composition including a thermal curing rubber component, wherein a static friction coefficient on a surface of the coating film is 0.5 or less, and wherein the sheath and the coating film are heated by infra-red light which is absorbed by the infra-red absorbing component to suppress uneven curing in the coating film such that an adhesion strength between the molded article main body and the coating film is about 0.44 MPa or more, and wherein a content of the at least one of titanium oxide and carbon is 1.0% by mass to 10% by mass per 100 parts by mass of a material of the sheath.

7. A method for manufacturing the molded article of claim 6 comprising a molded article main body, and a coating film covering a surface of the molded article main body, the coating film adhering to the molded article main body, the method comprising:

a process to prepare the molded article main body;

a process to coat a liquid rubber composition on a surface of the molded article main body and form a coating film; and a process to cure the coating film by heating the coating film by an infrared heater and form the coating film, wherein the molded article main body comprises a titanium oxide and the coating film comprises a rubber composition including a thermal curing rubber component, wherein a static friction coefficient on a surface of the coating film is 0.5 or less, and wherein an adhesion strength between the molded article main body and the coating film is about 0.44 MPa or more.

8. The cable according to claim 1, wherein the sheath comprises at least 90% rubber.

* * * * *